(12) United States Patent
Schneider et al.

(10) Patent No.: US 9,144,624 B2
(45) Date of Patent: Sep. 29, 2015

(54) METHOD FOR PROVIDING A LOCALIZED DWELL IN AN ADVANCING WEB

(71) Applicant: The Procter & Gamble Company, Cincinnati, OH (US)

(72) Inventors: Uwe Schneider, Cincinnati, OH (US); Paul Anthony Kawka, Kelso Township, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/330,341

(22) Filed: Jul. 14, 2014

(65) Prior Publication Data

US 2015/0020950 A1    Jan. 22, 2015

Related U.S. Application Data

(60) Provisional application No. 61/856,124, filed on Jul. 19, 2013.

(51) Int. Cl.
*A61L 15/16* (2006.01)
*B29C 65/08* (2006.01)
(Continued)

(52) U.S. Cl.
CPC ............ *A61L 15/16* (2013.01); *A61F 13/15764* (2013.01); *B29C 65/08* (2013.01); *B29C 65/78* (2013.01); *B65H 20/08* (2013.01);
(Continued)

(58) Field of Classification Search
CPC ...... B29C 65/08; B29C 65/088; B29C 65/78; B29C 66/1122
USPC .............. 156/64, 73.1, 73.4, 157, 502, 580.1, 156/580.2; 264/442, 443, 444, 445
See application file for complete search history.

(56) References Cited

U.S. PATENT DOCUMENTS 1,087,558 A    11/1912    Sears
2,723,620 A     8/1951    Huck
(Continued)

FOREIGN PATENT DOCUMENTS

CN    101245839    8/2008
DE    4301650 C1   1/1994
(Continued)

OTHER PUBLICATIONS

PCT/US2014/046650 International Search Report and Written Opinion dated, Oct. 27, 2014, 9 pages.
(Continued)

*Primary Examiner* — James Sells
(74) *Attorney, Agent, or Firm* — Sarah M. DeCristofaro

(57) ABSTRACT

A method for dwelling a portion of a web is disclosed. A web can be conveyed at a first velocity by an apparatus comprising a first traversing guide and a second traversing guide operatively connected in a fixed spatial relationship. The first traversing guide and the second traversing guide can be moveable from a start position in a substantially linear path. The first traversing guide and the second traversing guide can be moved in a first direction at a second velocity equal to about one half the first velocity for a dwell time. One or more processing stations can bond the at least two layers of the web. The first traversing guide and the second traversing guide can be accelerated and decelerated in a second direction opposite the first direction until the first traversing guide and the second traversing guide are returned to the start position in a return time.

20 Claims, 16 Drawing Sheets

(51) Int. Cl.
- *B29C 65/78* (2006.01)
- *A61F 13/15* (2006.01)
- *B65H 20/08* (2006.01)
- *B65H 20/24* (2006.01)
- *B65H 39/16* (2006.01)

(52) U.S. Cl.
CPC ............... *B65H 20/24* (2013.01); *B65H 39/16* (2013.01); *A61F 2013/15861* (2013.01); *B65H 2301/4491* (2013.01)

(56) References Cited

U.S. PATENT DOCUMENTS

| | | | |
|---|---|---|---|
| 3,093,069 | A | 6/1963 | Luehrs |
| 3,220,347 | A | 11/1965 | Luehrs |
| 3,280,737 | A | 10/1966 | Huck |
| 3,507,018 | A | 4/1970 | Mayfield et al. |
| 3,559,916 | A | 2/1971 | Hilscher |
| 3,605,506 | A | 9/1971 | Kuster |
| 3,613,978 | A | 10/1971 | Renold |
| 3,659,767 | A | 5/1972 | Martin |
| 3,763,717 | A | 10/1973 | Lenoir et al. |
| 3,796,360 | A | 3/1974 | Alexeff |
| 3,997,254 | A | 12/1976 | Yamada et al. |
| 4,011,976 | A | 3/1977 | Greer |
| 4,203,540 | A | 5/1980 | Giros |
| 4,244,504 | A | 1/1981 | Grob et al. |
| 4,292,856 | A | 10/1981 | Hamilton |
| 4,564,150 | A | 1/1986 | Keene et al. |
| 4,582,271 | A | 4/1986 | Takahashi |
| 4,601,387 | A | 7/1986 | Köbler |
| 4,698,918 | A | 10/1987 | Kotitschke et al. |
| 4,778,093 | A | 10/1988 | Renold |
| 4,793,564 | A | 12/1988 | Hank et al. |
| 5,163,594 | A | 11/1992 | Meyer |
| 5,277,571 | A | 1/1994 | Bringing |
| 5,373,761 | A | 12/1994 | Brining |
| 5,402,957 | A | 4/1995 | Evans |
| 5,407,513 | A | 4/1995 | Hayden et al. |
| 5,462,631 | A | 10/1995 | Gardner |
| 5,693,165 | A | 12/1997 | Schmitz |
| 5,716,478 | A * | 2/1998 | Boothe et al. ............... 156/302 |
| 5,746,869 | A | 5/1998 | Hayden et al. |
| 5,758,840 | A | 6/1998 | Murakami |
| 5,791,541 | A | 8/1998 | Jitsuish et al. |
| 5,825,374 | A | 10/1998 | Albertalli et al. |
| 6,050,517 | A | 4/2000 | Dobrescu et al. |
| 6,131,372 | A * | 10/2000 | Pruett ............................ 53/448 |
| 6,186,501 | B1 | 2/2001 | St. Ours |
| 6,293,453 | B2 | 9/2001 | Hirose et al. |
| 6,349,867 | B1 | 2/2002 | Fernfors |
| 6,596,108 | B2 | 7/2003 | McCabe |
| 6,616,026 | B1 | 9/2003 | Wittmaier |
| 6,705,499 | B1 | 3/2004 | Ruckmann et al. |
| 6,763,749 | B2 | 7/2004 | Droste et al. |
| 6,824,032 | B2 | 11/2004 | Kumatori |
| 6,830,212 | B1 | 12/2004 | Harris |
| 6,969,206 | B2 | 11/2005 | Iwanaga et al. |
| 8,377,249 | B2 | 2/2013 | Gill |
| 2003/0087740 | A1 | 5/2003 | Brinkmann et al. |
| 2011/0049210 | A1 | 3/2011 | Kameda |

FOREIGN PATENT DOCUMENTS

| | | |
|---|---|---|
| EP | 0 652 174 A1 | 11/1993 |
| EP | 0 510 251 A1 | 6/1995 |
| EP | 0 989 084 A2 | 3/2000 |
| EP | 1 302 424 A2 | 4/2003 |
| EP | 1 344 639 A2 | 9/2003 |
| EP | 2 105 281 | 9/2009 |
| GB | 1 065 161 A | 4/1967 |
| JP | 2253955 | 10/1990 |
| JP | 4197957 | 7/1992 |
| JP | 5286617 | 11/1993 |
| JP | 7315644 | 12/1995 |
| JP | 7315649 | 12/1995 |
| JP | 9079926 | 3/1997 |
| JP | 9142707 | 6/1997 |
| JP | 9328246 | 12/1997 |
| JP | 2002 234648 | 8/2002 |
| JP | 2004 075212 | 3/2004 |
| JP | 2004 091101 | 3/2004 |
| JP | 2004 115199 | 4/2004 |
| JP | 2004 161485 | 6/2004 |
| WO | WO 95/12491 | 5/1995 |
| WO | WO 95/12539 | 5/1995 |

OTHER PUBLICATIONS

PCT/US2010/029141 International Search Report and Written Opinion dated Jul. 27, 2010, 12 pages.

\* cited by examiner

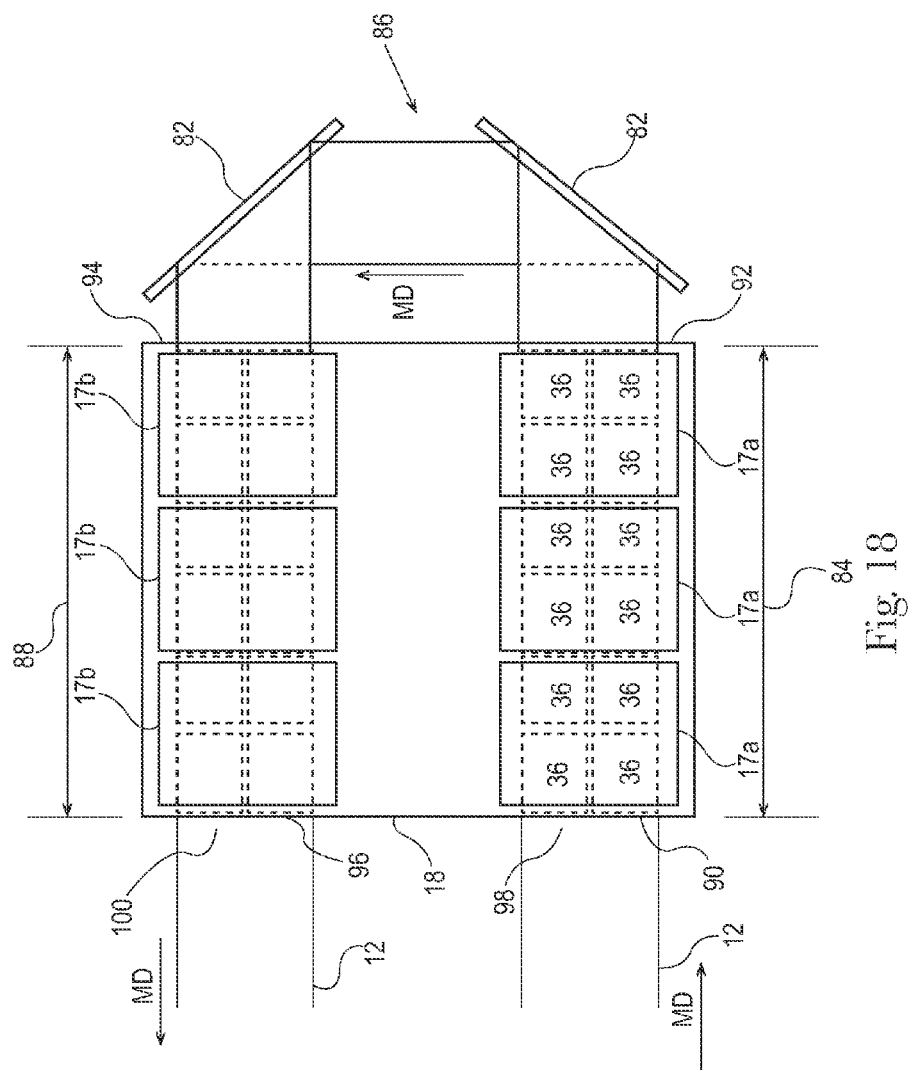

METHOD FOR PROVIDING A LOCALIZED DWELL IN AN ADVANCING WEB

CROSS REFERENCE TO RELATED APPLICATION

This application claims the benefit of U.S. Provisional Application No. 61/856,124 filed on Jul. 19, 2013, the substance of which is incorporated herein by reference.

FIELD OF THE INVENTION

The present disclosure relates to methods and apparatuses utilizing continuous substrates for manufacturing articles, and more particularly, to methods and apparatuses for providing a localized dwell in an advancing web.

BACKGROUND OF THE INVENTION

Along an assembly line, various types of articles, such as for example, diapers and other absorbent articles, may be assembled by adding components to and otherwise modifying and advancing, continuous webs of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, top sheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for attaching different components to an advancing web. Some production operations are configured to advance substrates in a machine direction at a constant speed. However, when advancing webs have components added thereto or are otherwise subjected to processing operations during production, it may be necessary to slow or stop the advancing web. For example, it may be necessary to slow or stop an advancing web passing through a processing station configured to perform such operations as, for example, gluing, welding, and adding discrete components. In an attempt to avoid having to vary the speed of the entire length of a substrate passing through an assembly line, some devices can be used to vary the speed of a portion of the substrate without affecting the speed of the entire substrate. However, such devices may only be configured to slow or stop the portion of the advancing web passing through a processing station for an instant or a very short duration of time, such as the time to process one single product. In turn, the processing stations may not be able to complete their respective functions during the relatively short time period while the web is slowed or stopped.

Other attempts have been made to process an advancing web such that the overall manufacturing line speed is not affected. For example, devices that shuttle the processing equipment at the speed of the web during processing and index the shuttle back to again process with the speed of the web have been developed. Due to the shuttling, which includes abrupt directional changes both horizontally and vertically, these devices are limited to smaller sizes and lighter weights. Further, these devices are limited as to how fast they can be shuttled; transferring a device at a high speed with high mass is difficult to control.

Still further, as the demand for consumer products increase, manufacturers are faced with having to produce products faster or at higher manufacturing throughput speeds. Thus, equipment is being developed which requires greater web handling capability. Accordingly, a need exists for a device that can suspend a portion of an advancing web for a predetermined dwell time, thereby keeping the web stationary for a time period longer than required to process a single product. For example, an apparatus is needed to stop a constantly advancing web at a gluing station so that three products can be glued and subsequently transported such that the line speed downstream of the apparatus is maintained. As previously stated, various methods and apparatuses have been developed to handle changing the web speed such that a fast operation, such as gluing or welding, that takes substantially less time than the period of one product, can be performed on one or more products. However, the current apparatuses are unable to handle a web such that one or more processes can be performed on the web over a time period greater than the time it takes to discharge one product from the complete manufacturing process. Stated another way, the current apparatuses are unable to handle processing a web for longer than the time allotted to move one product through the apparatus to maintain the desired line-speed downstream of the apparatus. Thus, a need exists for a device to handle the web such that more than one process can be performed on the web such that two or more products are processed simultaneously at zero speed for a time period longer than the time period required to process one product without affecting the overall speed of the web in subsequent manufacturing operations.

SUMMARY OF THE INVENTION

A method for producing a localized dwell in a portion of a web is disclosed. The method includes the following steps. One or more webs can be conveyed at a first velocity in a machine direction, wherein the one or more webs are conveyed by an apparatus comprising a first traversing guide and a second traversing guide. The first traversing guide and the second traversing guide can be operatively connected in a fixed spatial relationship. The first traversing guide and the second traversing guide can be moveable from a start position in a substantially linear path. The first traversing guide and the second traversing guide can return to the start position after an operation cycle in a cycle time. The first traversing guide and the second traversing guide can be moved in a first direction at a second velocity equal to about one half the first velocity for a dwell time. The one or more webs can be bonded, wherein the bonding is performed at one or more processing stations. The first traversing guide and the second traversing guide can be accelerated and decelerated in a second direction opposite the first direction until the first traversing guide and the second traversing guide are returned to the start position in a return time. The return time can be equal to the difference between the cycle time and the dwell time, and the dwell time is greater than one product period.

BRIEF DESCRIPTION OF THE DRAWINGS

FIG. 18 is a schematic representation of one or more processing stations and one or more turn bars to direct one or more webs in accordance with one non-limiting embodiment of the present invention.

DETAILED DESCRIPTION OF THE INVENTION

Aspects of the present disclosure involve methods and apparatuses utilizing continuous webs for manufacturing articles, and more particularly, methods and apparatuses for varying the speed of an advancing web. Particular embodiments of the apparatuses and methods disclosed herein provide for localized speed changes of an advancing web. As discussed below in more detail, embodiments of a localized speed varying apparatus can include, for example, first and second fixed guides, first and second traversing guides, and at least two variable speed guides positioned upstream and downstream of a processing station, and an actuator for moving a sled operatively connected between the first and second traversing guides. The motion of the sled changes the length of a portion of the advancing web upstream and downstream of the processing station in a cyclic fashion. The changes in web length between the fixed speed guides and the traversing guides can result in localized speed changes of the web and at least a momentary dwell in the web. Coordination between the traversing guides allows for localized speed changes of the web passing through the processing station without affecting the speed of the web upstream of the first fixed guide and downstream of the second fixed guide.

As mentioned above, apparatuses and methods of the present disclosure may be utilized to change the speeds of continuous webs used in the manufacture of absorbent articles. Such webs may be utilized in absorbent article components such as, for example: backsheets, topsheets, absorbent cores, front and/or back ears, fastener components, and various types of elastic webs and components such as leg elastics, barrier leg cuff elastics, and waist elastics. In addition, webs may include continuous webs of material, such as laminates. It is to be appreciated that the apparatuses and methods disclosed herein may be applied to the manufacture of many different types of articles and products manufactured from one or more webs. Examples of other articles, products, and processes include bonded laminate consumer products, packaging components, labels, and metal processing. More specifically, for example, a product such as a cleaning wipe comprising one or more layers of webs including layers of liquid permeable webs and a core between one or more layers of the webs can be bonded along the outer edge and/or throughout the product using the process disclosed herein.

Figure 1:
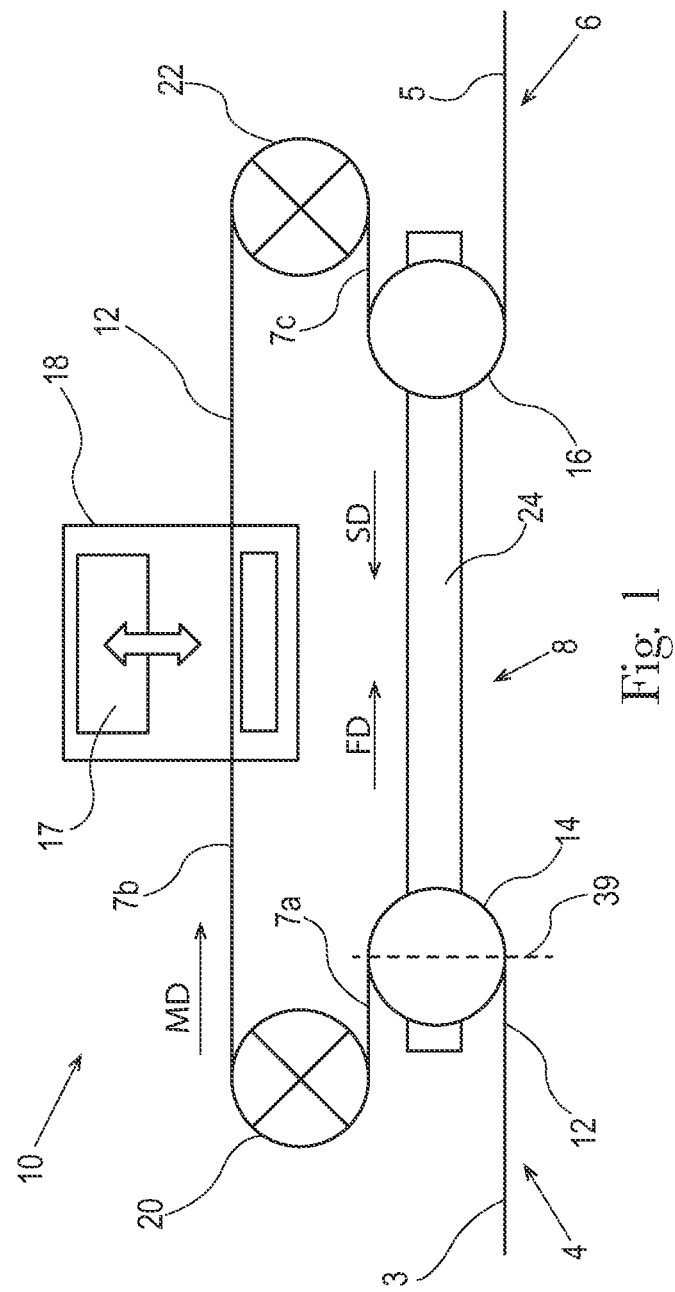
FIG. 1 is a schematic representation of an apparatus to dwell and process one or more webs in accordance with one non-limiting embodiment of the present invention.
Figure 2:
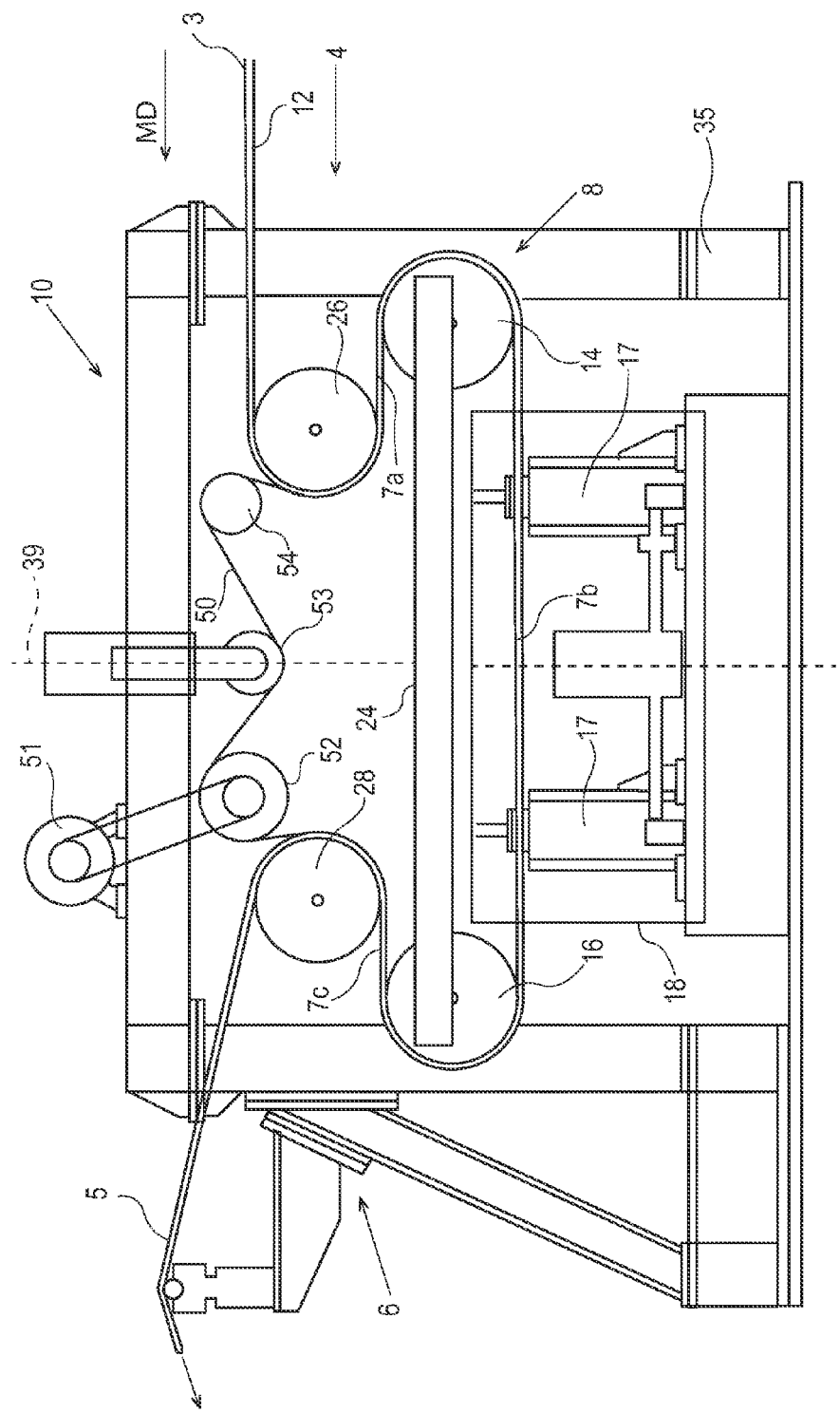
FIG. 2 is a schematic representation of an apparatus to dwell and process one or more webs in accordance with one non-limiting embodiment of the present invention.

FIGS. 1 and 2 illustrate a side elevation view of a schematic representation of representative apparatuses 10 for making a product requiring the manufacturing of one or more webs 12, and more specifically, for changing the localized speed of one or more webs 12 for processing. The web 12 can be a substantially flexible substrate that can be transported along a curvilinear trajectory and will adapt its shape so as to conform to the trajectory via a series of traversing guides, which can be can be any device about which a web 12 can rotate, such as cylindrical rollers having a width at least equal to the width of the web being processed. The web can be formed of material such as paper, nonwoven materials, laminates, airfelt, plastic, and other similar materials. The web 12 is transported along upstream trajectory 3 with a constant velocity of transport, $V_0$ in the machine direction MD. One of ordinary skill in the art would understand that $V_0$ can be changed as desired, such as for line start-ups and alterations in manufacturing speeds. As depicted in FIG. 1, the upstream trajectory 3 is formed by the length of the web 12 which extends to the left of the first traversing guide 14, and which is moving toward the in-feed side 4 of the apparatus 10. As depicted in FIG. 2, the upstream trajectory 3 is formed by the length of the web 12 which extends to the right of the first fixed guide, and which is moving toward the in-feed side 4 of the apparatus 10. After passing through the apparatus 10, the web 12 exits at the out-feed side 6 and is transported at constant velocity $V_0$ along the downstream trajectory 5, which, as depicted in FIG. 2, for example, extends to the left of the second fixed guide 28 and/or the second traversing guide 16. The upstream and downstream trajectories 3, 5 generally correspond to the machine direction MD, and can be formed by straight line or curvilinear paths. As referred to herein, the term velocity can refer to the numerical magnitude of the velocity, also known as the speed, which has no directional component.

Referring to FIG. 1, the web 12 can be fed through the apparatus 10 such that a processing station 18 can act on the one or more webs 12. The processing station 18 can perform a bonding operation that can include, for example, gluing or welding. More specifically, bonding layers of the one or more webs 12 requires that the one or more webs 14 stop for a predetermined dwell time. The dwell time is at least the time required to bond one or more webs 12, referred to as the bonding time. The processing station 18 acts on the one or more webs 12 for a bonding time which may be equal to or less than the dwell time. Thus, to achieve this dwell time, the apparatus 10 comprises a traversing assembly 8. In one embodiment, the traversing assembly 8 can comprise a first traversing guide 14, a second traversing guide 16, and a sled 24. The first traversing guide 14 and a second traversing guide 16 can be upstream and downstream, respectively, of the processing station 18, and, in this example embodiment, upstream and downstream of a first variable speed guide 20 and a second variable speed guide 22, respectively. The first traversing guide 14 and the second traversing guide 16 can be operatively connected by a sled 24. The sled 24, as illustrated in FIG. 1, can be any device that provides a fixed connection between the first traversing guide 14 and the second traversing guide 16. The connection can include a physical, mechanical connection and/or an electrical, non-physical connection, between the first traversing guide 14 and the second traversing guide 16. The physical, mechanical connection can be a simple rigid connector to which traversing guides are mounted in fixed relation to each other. For example, the sled 24 can be a rigid bar made from aluminum. However, the sled 24 can also comprise an electrical, non-physical, connection, such as where the first traversing guide 14 and the second traversing guide are mechanically driven independently but can be connected electronically so that the first traversing guide 14 and the second traversing guide 16 can communicate with one another and, thus, can move in relation to one another. For purposes of clarity, most of the Figures illustrated in the present disclosure show the sled 24 as being a mechanical connection.

Still referring to FIG. 1, the traversing assembly 8 can move in a cyclic back and forth motion, and can, in turn move the first traversing guide 14 and the second traversing guide 16 in a substantially cyclic motion, which can cause the two or more webs 12 to dwell for processing at the processing station 18, which is in a localized area of the apparatus 10. The cyclic back and forth motion of the traversing assembly 8 can be a substantially linear motion that is substantially parallel to the machine direction MD of second section 7b of the web 12. Alternatively, the cyclic motion of the traversing assembly 8 can be a curvilinear motion so long as the sled 24 and/or the first traversing guide 14 and the second traversing guide 16 move to take up the web 12 such that second section 7b can dwell, also referred to as being stationary, for a predetermined time.

The sled 24 can move from a start position 39 in a first direction FD, which can be in the same direction as the machine direction MD for apparatus configurations as illustrated in FIG. 1. In general, the first direction FD is in a direction that results in first section 7a of the web increasing in length. During the time sled 24 is in motion in the first direction FD, the web(s) 12 experience a decreased velocity in second section 7b between variable speed guide 20 and variable speed guide 22. In general, for a web 12 moving at a velocity of $V_0$ at the in-feed side 6, the traversing assembly 10 can move a velocity of $V_0/2$ to dwell the web(s) 12 at second section 7b, the web wrap of each of variable speed guide 20 and first traversing guide 14 should result in the webs being substantially parallel to one another. That is, with reference to FIG. 1, the portion of the web(s) in upstream trajectory 3 and web portion 7a should be parallel to each other and parallel to the motion of the sled 24. Likewise, the portion of web(s) 12 in downstream trajectory 5 and web portion 7c should be parallel to each other and parallel to the motion of the sled 24. When the portion of the web(s) 12 in the area of the upstream trajectory 3, first section 7a, downstream trajectory 5 and third section 7c are configured to be substantially parallel, traversing assembly 8 can move in the first direction FD at a speed of $V_0/2$ so that the webs 12 can reach a velocity of zero in second section 7b between variable speed guide 20 and variable speed guide 22; thus, presenting a stationary web for processing in the area of the processing station 18. This web stoppage is referred to herein as dwell. Generally, the one or more webs 12 can dwell for a dwell time substantially equal to, or longer than, the bonding time, in a localized area referred to as second section 7b.

The bonding time is the time required to perform a process, such as welding, on the one or more webs 12. More specifically, the bonding time is a predetermined time based on the material properties of the layers of the one or more webs 12 and the type of processing unit 17, housed within a processing station 18. The processing unit 17 can be an ultrasonic bonder, thermal bonding unit, mechanical compression device, or other bonding device. For example, for an ultrasonic processing unit 17 the bonding time can comprise a time period for energy entry and a time period for material compression, which can happen sequentially or simultaneously. Generally, the properties of the one or more webs 12 can change the bonding time. For example, generally, the greater the basis weight of the one or more webs 12 the greater the bonding time. Further, one of ordinary skill in the art would understand that the chemical composition of the one or more webs 12 can also effect the bonding time. The dwell of the one or more webs 12 will be discussed in more detail below.

Referring to FIG. 2, an example embodiment of an apparatus 10 for manufacturing two or more webs 12 is illustrated. The apparatus 10 comprises a first fixed guide 26 and a second fixed guide 28. The first fixed guide 26 and the second fixed guide 28 can be in a fixed position. The first fixed guide 26 and the second fixed guide 28 can be any device about which a web 12 can rotate, such as a roller. Guided by the first fixed guide 26, the one or more webs 12 can be looped around an upstream first traversing guide 14. Similarly, guided by the second fixed guide 28, the web 12 can be looped from a downstream second traversing guide 16. The apparatus 10 can also comprise a traversing assembly 8. The traversing assembly can comprise a first traversing guide 14 and a second traversing guide 16 that can be operatively connected to a sled 24. As stated above, the sled 24 can be any device, mechanical and/or electrical, that allows the first traversing guide 14 and the second traversing guide 16 to move in fixed relation to each other. In general, sled 24 will allow the first traversing guide 14 and the second traversing guide 16 to move in a coordinated, linear manner. The traversing assembly 8 can be linearly translated along the frame 35 or, stated another way with respect to the embodiment depicted in FIG. 2, substantially parallel to the machine direction MD, in a substantially linear, cyclic fashion. The motion of the traversing assembly 8 can be substantially linear because some slight vertical motion would not affect the processing of the one or more webs 12 in the area of the processing stations 18. Thus, how much vertical motion the traversing assembly 8 can undergo can be determined by the tolerance for movement of web(s) 12 in the area of the one or more processing stations 18.

Still referring to FIG. 2, intermediate trajectories of the web 12 can be located between the first fixed guide 26 and the second fixed guide 28. More specifically, the first section 7a can be located between the first fixed guide 26 and the first traversing guide 14, the second section 7b can be located between the first traversing guide 14 and the second traversing guide 16, and the third section 7c can be located between the second traversing guide 16 and the second fixed guide 28. Due to the symmetry of the apparatus 10, an increase in length of the first section 7a, upon displacement of the sled 24 in a first direction, which in the configuration depicted in FIG. 2 is in a direction opposite the machine direction MD, away from a start position 39, will result in a decrease in the length of the web in the third section 7c equal to the length increase of section 7a, and vice versa. The length of section 7b is constant.

When sled 24 moves in a first direction FD, the web(s) 12 in first section 7a increase in length and the web(s) 12 located in the second section 7b can be stationary for a predetermined time (also referred to as dwell time). During the time the web is stationary, the one or more processing units 17 housed within the processing station 18 can operate on the one or more webs 12. In one example embodiment, the processing units 17 can comprise a pair of vertically displaceable devices which can impart pressure onto the web 12 such that at least a portion of the layers of the one or more webs 12 become bonded. After the processing units 17 have operated on the one or more webs 12, the sled 24 operatively engaging the first traversing guide 14 and the second traversing guide 16 can be accelerated in a second direction SD, which in the apparatus configuration depicted in FIG. 2 corresponds to the machine direction MD, toward the downstream trajectory 5 with a web speed of less than or equal to about 2 $V_0$. The velocity of the processed web downstream of the first traversing guide 14 can be generally less than 2 $V_0$ for processing products for dwells substantially shorter than the manufacturing period for one product. The velocity of the web can increase based on an increase in the dwell for product processing in second section 7b.

Still referring to FIG. 2, the first fixed guide 26 and the second fixed guide 28 and the first traversing guide 14 and the second traversing guide 16 can be cylindrical rollers driven by a drive member in the form of a closed loop 50 and pulleys 52, 53, and 54. The loop 50 is driven at a constant speed which is equal to the speed of transport $V_0$, of the web 12 by a single drive motor 51. By driving the first fixed guide 26, the second fixed guide 28, the first traversing guide 14, and the second traversing guide 16, the strain exerted on the web 12 is minimized and can be limited to the acceleration forces, which are acting to change the speed of the web. One of ordinary skill in the art would understand the closed loop 50 can be used on any embodiment of this disclosure to reduce the strain exerted on the one or more webs 12.

As previously stated, the first traversing guide 14 and the second traversing guide 16 can move in a substantially linear direction that is substantially parallel to the machine direction of the web 12 in the second section 7b and the web 12 can enter the in-feed side 4 at a constant velocity $V_0$. In order to process a portion of the web 12 at the one or more processing stations 18 the web 12 needs to remain stationary, that is having a web speed of zero, for the bonding time, which, as previously stated, is the time to process the one or more webs 12. Thus, with respect to the configuration shown in FIG. 2, from its start position 39, the first traversing guide 14 and the second traversing guide 16 can move opposite the machine direction MD in a substantially linear manner. More specifically, the sled 24, operatively connecting the first traversing guide 14 and the second traversing guide 16, could move in a first direction, opposite the machine direction MD, at a velocity of $V_0/2$ in order to take up or to increase the length of the one or more webs 12 in first section 7a the web(s) 12 being fed from the in-feed side 4 at a velocity of $V_0$. Stated another way, as the sled 24 moves in a first direction opposite the machine direction MD at a velocity of $V_0/2$, the length of the first section 7a will increase by $V_0/2$ times the bonding time. As stated above, if the geometry of the first section 7a, and the second section 7b is other than substantially parallel, the sled 24 will have to move at a velocity of other than $V_0/2$ to dwell the web(s) 12 in second section 7b. Generally, during the time the sled 24 moves in the first direction, the net displacement of the web 12 along the second section 7b can be zero, i.e., the web is stationary. However, if the sled 41 moves at a speed that is slower than $V_0/2$ then the web 12 in second section 7b is slowed down but is not stationary. Similarly, if the sled 24 moves at a speed that is faster than $V_0/2$, then the web 12 in second section 7b is reversed (the web 12 moves in a direction opposite the machine direction MD).

Figure 3:
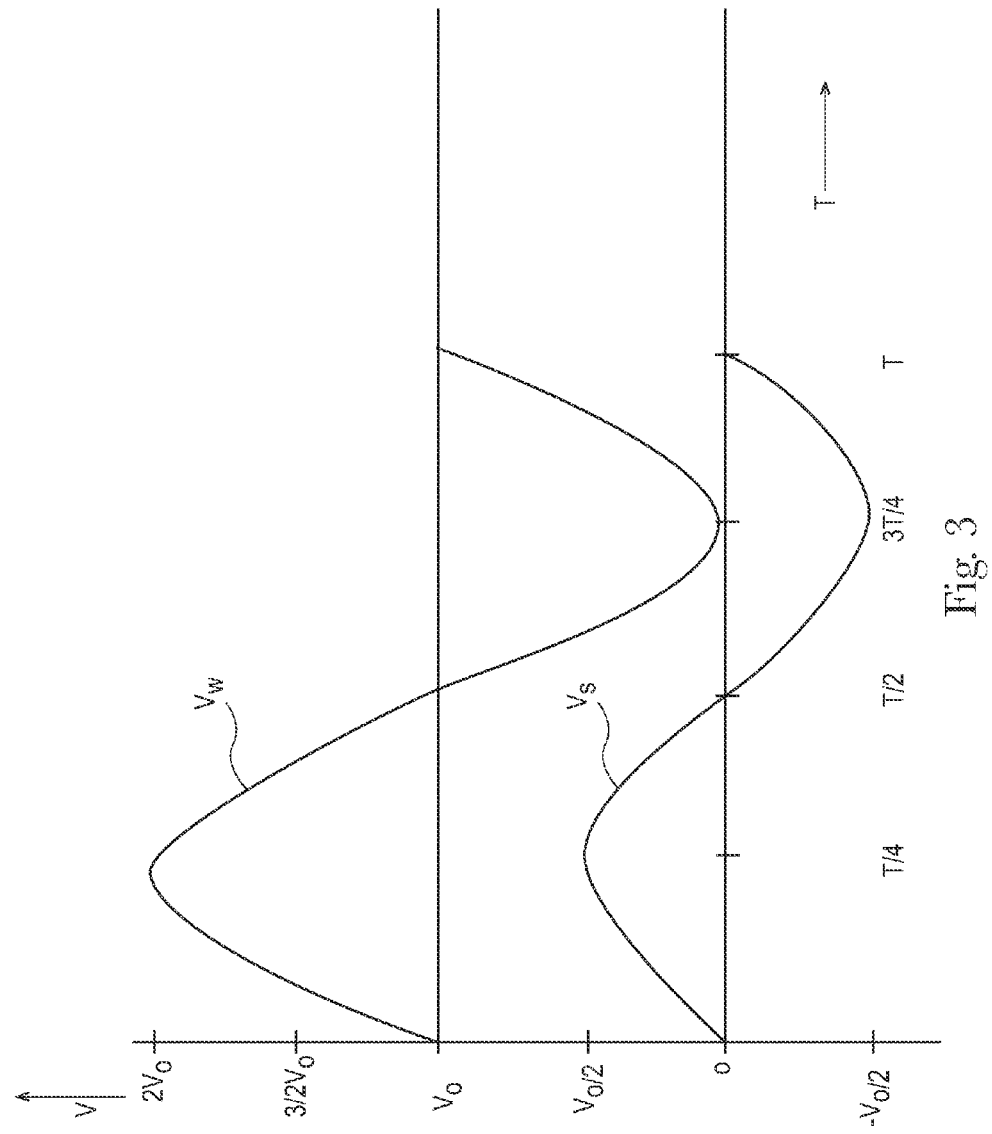
FIG. 3 is a graph of the velocity profile of the one or more webs and the velocity profile of the sled over a given period of time.

After processing is complete on the layers of the one or more webs 12, the sled 24 can move in a second direction SD to return to the start position 39. FIG. 3 graphically illustrates the velocity profile of the sled 24 and the velocity profile of the web 12 for the apparatus 10 illustrated in FIG. 2 and assumes the apparatus 10 processes a single, individual product, which can be accomplished with the back and forth cyclic motion of sled 24 that corresponds to a sinusoidal velocity profile. The web velocity $V_w$ along the second section 7b is indicated by line $V_w$. The web velocity $V_w$ starts an operation cycle equal to $V_0$, which is the velocity of the one or more webs 12 as the one or more webs 12 enter the in-feed side 4 of the apparatus 10, when the sled 24 is in the start position 39. However, the web velocity $V_w$ can be dependent on the movement of the sled 24. As shown in FIG. 3, the web velocity $V_w$ in section 7b can change based on the sled velocity $V_s$, in indicated by line $V_s$. As stated above, the sled 24 can begin a cycle in a start position 39. When the sled 24 is at the start position 39, the web 12 has a web velocity of $V_0$, the speed of the incoming one or more webs 12 from the in-feed side 4 of the apparatus 10. As the sled 24 moves from the start position 39, sled velocity $V_s$ of zero, in a first direction FD to a sled velocity of $V_0/2$, the web velocity $V_w$ will decrease from a web velocity of $V_0$ to substantially zero. The sled 24, operatively engaging the first traversing guide 14 and the second traversing guide 16, can then travel in a second direction SD (opposite the first direction FD) to return to start position 39. The sled velocity $V_s$ can increase from substantially zero to $V_0/2$. During this time, the web velocity $V_w$ can increase from substantially zero to 2 $V_0$. As the sled 24 approaches the start position 39 the web velocity $V_w$ can approach $V_0$ and the sled velocity $V_s$ can approach zero.

The example embodiments shown in FIGS. 1 and 2 assume the processing occurs in a momentary dwell corresponding to the substantially instantaneous change in velocity of the sled 24. Stated another way, the sled 24, starting from the start position 39 and being driven by a circular rotating drive (as disclosed in U.S. Pat. No. 5,693,165 to Schmitz), can be moved according to a sinusoidal velocity profile as shown in FIG. 3. The disclosure regarding FIG. 3 above describes this cycle in terms of the web velocity $V_w$ and the sled velocity $V_s$, both of which vary in time sinusoidally. During an operation cycle, the sled 24 controls the web speed in localized areas, such that a first product is moved into the area of the processing unit 18 and after stopping the web for processing of the first product, the first product is moved out and a second product is moved into the processing unit 18 and so on and so forth. It has been contemplated to further increase manufacturing output by processing more than one product in one or more processing stations 18 during a cycle of the sled 24, which can require a more than instantaneous dwell time or, stated another way, more than the time required to process one product.

To dwell for a time longer than the time required to discharge a single product from the out-feed side 6 of the apparatus 10 while still maintaining the overall speed of the one or more webs 12 entering from the in-feed side 4 and exiting from the out-feed side 6 of the apparatus 10, it is necessary to process more than one product in an operation cycle. Thus, the apparatus 10 must operate such that the traversing assembly 8 moves according to a different velocity profile (than that of a sinusoidal velocity profile as described above) to account for the longer dwell in the one or more webs 12 for processing and for maintaining the velocity of the web(s) 12 such that when the one or more webs 12 exit the apparatus 10 from the out-feed side 6, the one or more webs 12 can be at a velocity that matches that of the manufacturing line.

Figure 4:
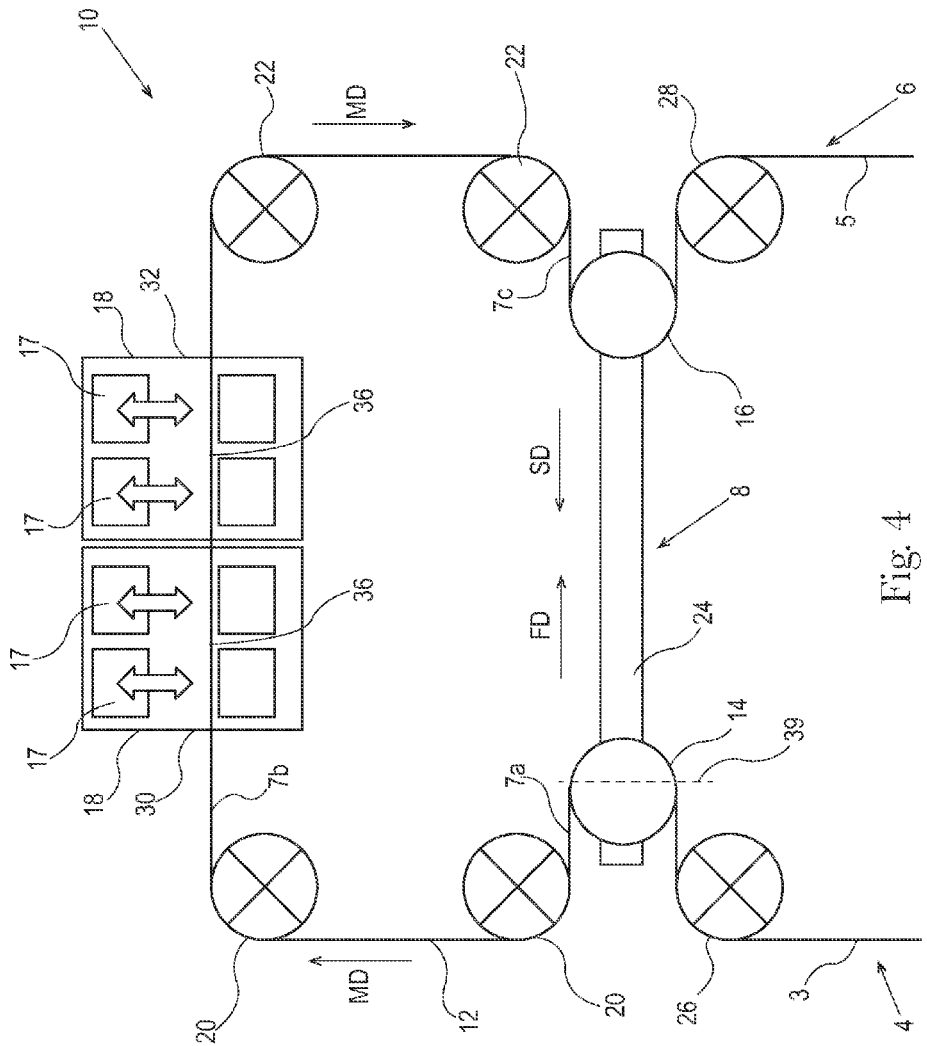
FIG. 4 is a schematic representation of an apparatus to dwell and process one or more webs in accordance with one non-limiting embodiment of the present invention.

In another example embodiment, shown in FIG. 4, an apparatus 10 for manufacturing two or more webs 12 can comprise two or more processing stations 18. Each processing station 18 can comprise one or more processing units 17 that can perform the same or different operations on the webs 12. For example, the first, upstream processing station 18 can comprise a processing unit 17 that thermally deforms the webs 12 and a second, subsequent processing unit 17 that performs an ultrasonic bonding operation on the layers of the one or more webs 12. The processing stations 18 can perform their respective operations in unison or at different times. Independent of the operation performed, the one or more webs 12 should dwell for the period of time required for the processing stations 18 to act on the layers of the one or more webs 12. As previously stated, each processing station 18 requires a bonding time, which is the longest period of time for all processing stations 18 to act on the one or more webs 12. Stated another way, the bonding time can be the elapsed time from the start of any processing by any processing station 18 till the end of all processing by any processing station 18. Therefore, the apparatus 10 must dwell, that is, render stationary, the web 12 for at least the bonding time. Stated another way, the traversing assembly 8 can dwell the one or more webs 12 by moving in a first direction, opposite the MD, for the bonding time, as illustrated in FIG. 4. For example, if two or more processing stations 18 act in unison (i.e., a first and second processing station start to process the one or more webs 12 at substantially the same point in time), the bonding time can be the time elapsed from when the first and second processing stations being to process the one or more webs 12 until the time that both processing stations are done acting on the one or more webs 12. Thus, the web 12 could be required to dwell for the time it takes for the first processing station and the second processing station to act.

Figure 5:
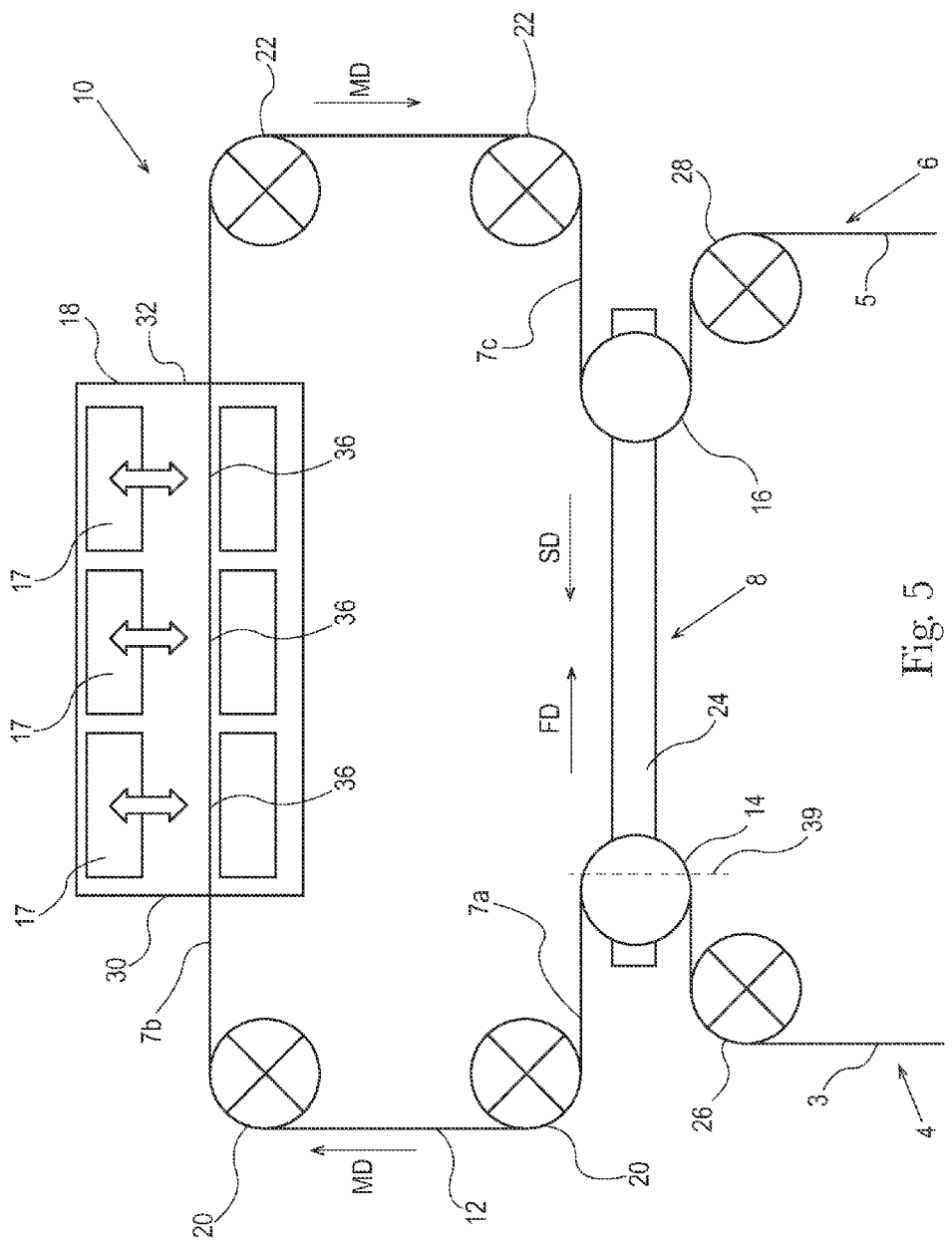
FIG. 5 is a schematic representation of an apparatus to dwell and process one or more webs in accordance with one non-limiting embodiment of the present invention.

As previously stated, the apparatus can comprise a first variable speed guide 20 and a second variable speed guide 22. As shown in FIGS. 4 and 5, there can be more than one first variable speed guide 20 upstream of the one or more processing stations 18 and downstream of the first traversing guide 14, and there can be more than one second variable speed guides 22 downstream of the one or more processing stations 18 and upstream of the second traversing guide 16. The first variable speed guide 20 and the second variable speed guide 22 can be in a substantially fixed position such that each guide does not move linearly during operation of the apparatus 10. Rather, the first variable speed guide 20 and the second variable speed guide 22 can each move rotationally about a fixed axis to guide the web(s) 12 from the first traversing guide 14, to the second traversing guide 16, and/or through the one or more processing stations 18. The first variable speed guide 20 and the second variable speed guide 22 can be any device about which a web 12 can rotate, such as a cylindrical roller. In one embodiment, the surface speed of the one or more first variable speed guides 20 and the one or more second variable speed guides 22 is variable. The variable surface speed of the guides 20, 21 can allow the first traversing guide 14 and the second traversing guide 16 to control the velocity of the web 12 in localized areas, such as second section 7b. The one or more first variable speed guides 20 and the one or more second variable speed guides 22 can aid in positioning the web 12 to, for example, enter and exit the one or more processing stations 18 and stop for a predetermined amount of time in the processing station, without altering the upstream or downstream constant velocity of $V_0$.

The apparatus 10 can further comprise at least a first fixed guide 26 and a second fixed guide 28. The first fixed guide 26 can be located upstream of the first traversing guide 14. The second fixed guide 28 can be located downstream of the second traversing guide 22. The first fixed guide 26 and the second fixed guide 28 can be driven or undriven cylindrical rollers that remain in a fixed position such that each guide does not move relative to the apparatus 10 during operation of the apparatus 10. Rather, the first fixed guide 26 and the second fixed guide 28 can move rotationally about a fixed axis to guide the one or more webs 12 onto the first traversing guide 14 or away from the second traversing guide 16. The first fixed guide 26 and the second fixed guide 28 can be any device about which a web 12 can rotate, such as a cylindrical roller. In another embodiment, a series of fixed guides can be placed upstream of the first traversing guide 14 and downstream of the second traversing guide 16 to aid in handling the one or more webs 12 during operation. The first fixed guide 26 and the second fixed guide 28 can be driven to provide a web speed having a constant velocity, $V_0$. In another embodiment, the apparatus can comprise one or more first fixed guides 26 and one or more second fixed guides 28, not shown.

Similar to the above, as illustrated in FIGS. 4 and 5, the one or more webs 12 can be fed around a portion of the first fixed guide 26 and the first traversing guide 14. The web(s) 12 enters the apparatus 10 at an initial, constant velocity of $V_0$. The traversing assembly 8 travels in a first direction FD away from the first fixed guide 26 and/or the in-feed side 4 of the apparatus 10 at a first velocity of $V_0/2$. As illustrated in FIGS. 4 and 5, the traversing assembly 8 can move in a substantially linear path. However, the traversing assembly can also move in a curvilinear path so long as the one or more web 12 is taken up at a rate which causes the one or more web(s) 12 in second section 7b to dwell. More specifically, the one or more first variable speed guides 20 and the one or more second variable speed guides 22 allow the traversing assembly 8 to move in a curvilinear path because the second section 7b of the one or more webs 12 would be unaffected by the movement or, stated differently, the second section 7b would remain substantially linear despite the curvilinear movement of the traversing assembly 8.

As the traversing assembly 8 travels in the first direction, the one or more webs 12 can be said to dwell such that the web velocity $V_w$ reaches zero in second section 7b. The web velocity $V_w$ can be zero for the bonding time, as described in the aforementioned. After the one or more processing stations 18 act on the one or more webs 12, or, stated another way, after the bonding time, the one or more processed webs 12 can be accelerated out of the area of the processing stations 18. The traversing assembly velocity $V_s$ upon completion of the bonding time reaches zero. At the time the traversing assembly velocity $V_s$ is zero, the web velocity $V_w$ will be equal to the initial velocity of the incoming one or more webs 12, $V_0$. The traversing assembly 8 comprising the first traversing guide 14 and the second traversing guide 16, operatively connected by the sled 24, can move in a second direction SD, opposite the first direction FD and/or away from the out-feed side 6 of the apparatus 10. The return time is the time it takes for the traversing assembly 8 to return to the start position 39 from a position other than the start position 39 after the bonding time.

The bonding time and the return time are related to the operation cycle which occurs in a cycle time. The cycle time, as previously stated, is the elapsed time from when the sled 24 departs from a start position 39 in order to dwell the web 12 to when the sled 24 reverses direction and returns to the start position 39.

Figure 6:
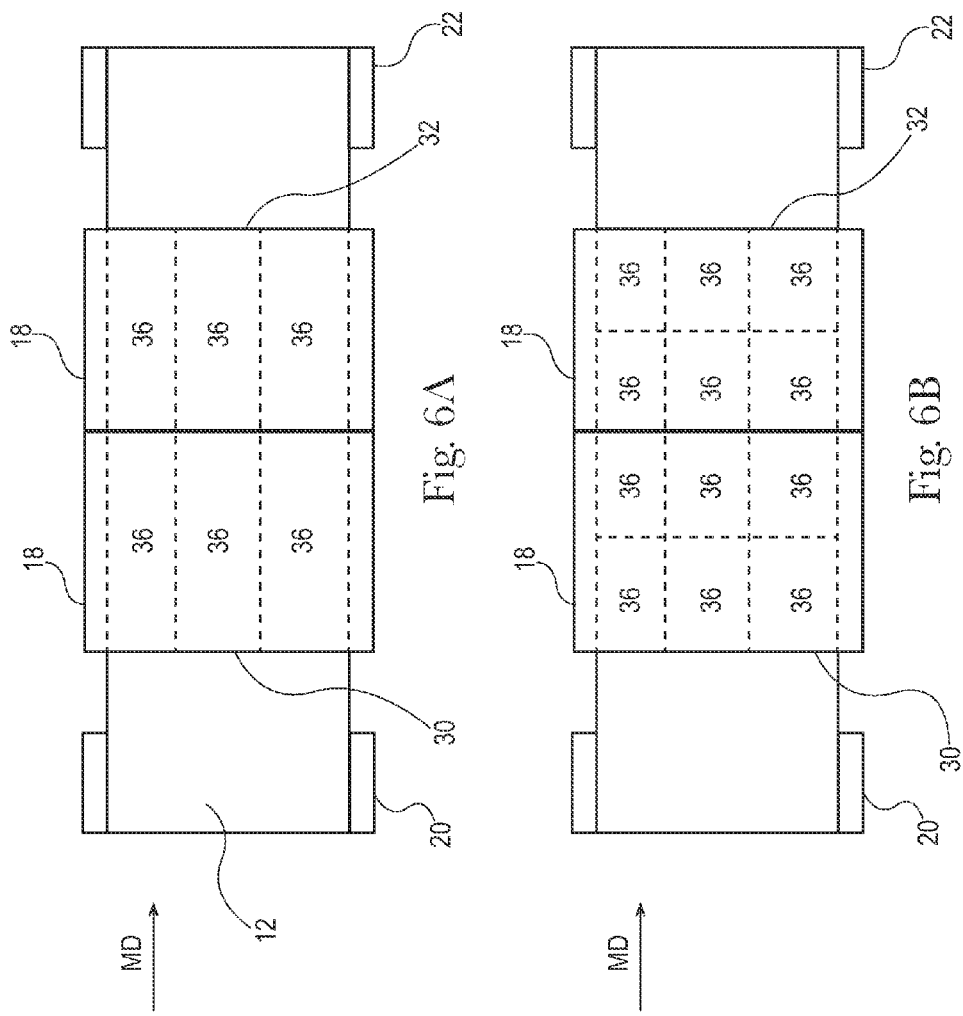
FIGS. 6A-B is a schematic representation of a processing station and one or more webs comprising products in accordance with one non-limiting embodiment of the present invention.

Referring to FIGS. 6A and 6B, the apparatus 10 can process one or more products 36 on the one or more webs 12 during a cycle time of the traversing assembly 8. FIG. 6A illustrates an array of six products 36 to be processed by one or more processing stations 18. Similarly, FIG. 6B illustrates an array of twelve products 36 to be processed by one or more processing stations 18. The cycle time, as previously described, can be the bonding time plus the return time. However, the cycle time can be governed by the manufacturing line speed at the out-feed side 6 of the apparatus 10. Thus, the time required to processes more than one product 36 while maintaining the manufacturing line velocity of the downstream trajectory 5 at the out-feed side 6 of the apparatus 10 is captured by the product period. The product period can be defined as the average time interval for one product 36 to leave the out-feed side 6 of the apparatus 10. For example, in a three-lane (substantially perpendicular to the MD) by two-wide (MD) operation, six products 36 would leave the apparatus 10 during six product periods, as shown in FIG. 6A. In order for six products 36 to be processed in a stationary process and to maintain the integrity of the one or more webs 12 (to avoid breaking or other damage from strain), the operation cycle must complete in a cycle time equal to the number of products being processed simultaneously (six) times the product period.

For example, the manufacturing line downstream of the out-feed side 6 of the apparatus 10 can be moving at a rate of 600 parts per minute, which is equivalent to 10 products per second or 0.1 seconds per product. Secondly, the apparatus 10 can, for example, process six products in one operation cycle time (as depicted in FIG. 6A). Thus, six products per operation cycle times 0.1 seconds per product can allow for a total operation cycle time of 0.6 seconds per operation cycle. Stated another way, the traversing assembly 8 must perform an operation cycle, as disclosed above, in a cycle time of 0.6 seconds to ensure that one or more webs 12 downstream of the apparatus 10 do not break, but rather continue at the desired, predetermined manufacturing line rate.

Figure 7:
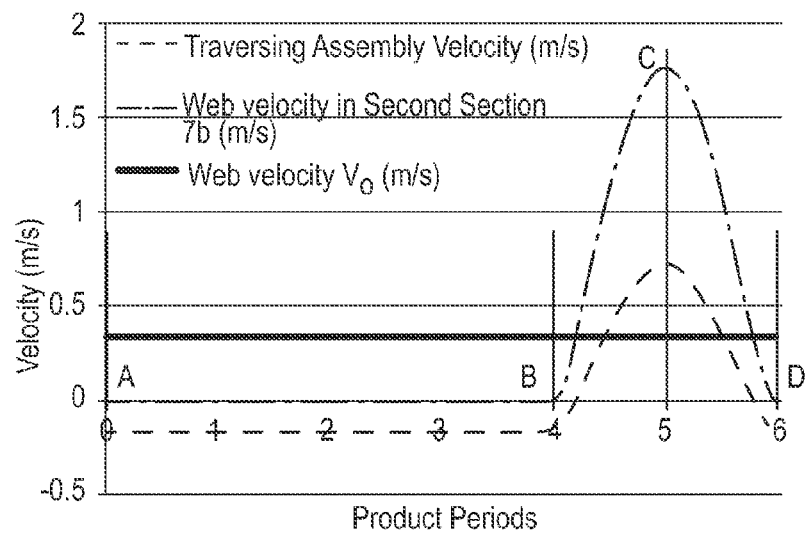
FIG. 7 is a graph of the velocity v. product period for the traversing assembly and one or more webs in accordance with one non-limiting embodiment of the present invention.

FIG. 7 graphically illustrates an example of the velocity profiles of the traversing assembly 8 and the one or more webs 12 that travel in an operation cycle. Still assuming the characteristics of the aforementioned example apply, six products can be processed by the processing station 18 during an operation cycle time. As previously stated, the bonding time is a predetermined time based on the characteristics of the one or more webs 12 and the type of manufacturing equipment that is performing the processing on the one or more webs 12. For this example embodiment, the bonding time is a predetermined time of four product periods or 0.4 seconds. Thus, because the operation cycle has a cycle time of 0.6 seconds, the return time (the time for the traversing assembly 8 to travel back to the start position after the bonding time) is the cycle time minus the bonding time. In this example, the return time, indicated in FIG. 7 is two product periods or 0.2 seconds. Therefore, the traversing assembly 8 must appropriately accelerate and decelerate to reach the start position in 0.2 seconds (the return time).

Also shown in FIG. 7 is the velocity of the one or more webs 12 downstream and upstream of the first traversing guide 14 and the second traversing guide 16, respectively. The velocity of the one or more webs 12 in second section 7b can remain substantially constant due to the position and velocity of the traversing assembly 8. The traversing assembly 8 travels away from the start position 39 at a velocity, referred to as the second velocity, sufficient to take up the one or more webs 12 advancing from the upstream trajectory 3. In one embodiment, the second velocity can be equal to about $V_0/2$. This allows the first traversing guide 14 to take up the additional one or more webs 12 traveling in from the in-feed side 4 at a velocity of $V_0$, which is shown to be about 0.33 meters per second in FIG. 7.

Figure 8:
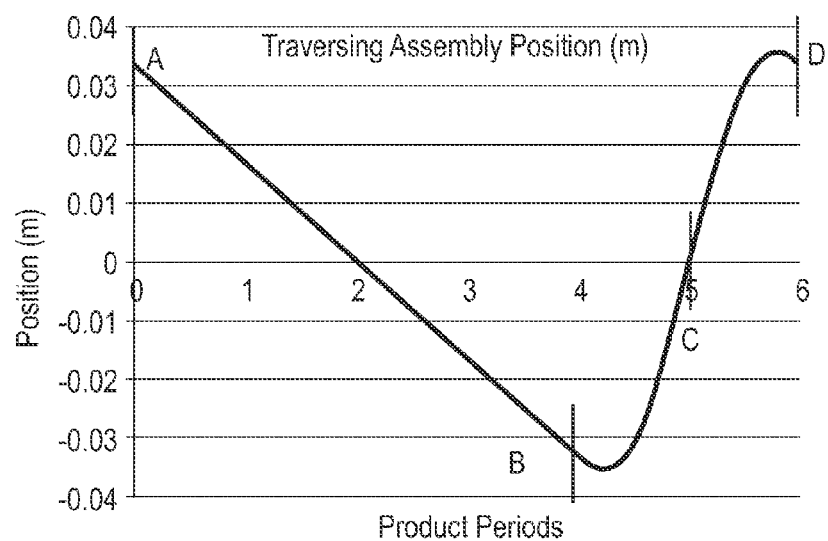
FIG. 8 is a graph of the position of the traversing assembly at a given product period in accordance with one non-limiting embodiment of the present invention.

More specifically, still referring to FIGS. 7 and 8, the traversing assembly 8 begins an operation cycle at a start position 39 (as shown, for example, in FIG. 5), which can be the position at which the traversing assembly 8 changes direction. The velocity of the traversing assembly 8 in the start position 39 is about zero and, thus, the velocity of the one or more webs 12 in second section 7b is about equal to the velocity of the one or more webs 12 in the upstream trajectory 3, which is $V_0$ (referred to as the first velocity). Once the operation cycle begins, the traversing assembly 8 can move in a first direction FD at a second velocity sufficient to take up the one or more webs entering through the in-feed side 4 of the apparatus 10 and to dwell, or render stationary, the one or more webs in second section 7b. The traversing assembly 8 can move in the first direction FD at the second velocity for the bonding time. At the end of the bonding time, the traversing assembly 8 will decelerate to reach a third velocity equal to zero. At the time of the traversing assembly 8 is decelerating, the one or more webs 12 will begin to accelerate in the second section 7b. Upon reaching zero, the traversing assembly 8 can change direction to move in a second direction, opposite the first direction. After the change in direction, the traversing assembly can accelerate, which allows the one or more webs 12 in the second section 7b to accelerate to two times the $V_0$. The traversing guide 8 will then begin to decelerate as it approaches the start position 39. During the deceleration of the traversing assembly 8, the one or more webs 12 also decelerate. However, at the end of the deceleration the traversing assembly 8 can be in a position other than the start position 39, as shown in FIG. 8. Thus, the traversing assembly 8 can be accelerated back to the start position 39. When the traversing assembly has reached the start position 39, the one or more webs 12 in second section 7b can again reach a velocity of $V_0$.

FIG. 8 illustrates the position of the traversing assembly 8 in relation to product periods for the aforementioned example. As shown in FIG. 8 the traversing assembly 8 moves at constant velocity of $V_0/2$ to accumulate the incoming one or more webs 12 and to dwell the one or more webs 12 present in second section 7b. As depicted, the traversing assembly 8 begins in some start position 39 and ultimately returns to the start position 39 at the end of six product periods (the operation cycle time). Intermittently, once the processing has completed at the end of the bonding time, or four product periods, the traversing assembly 8 must return to the start position in a mere two product periods in order to be in the start position 39 to being a second, subsequent operation cycle.

Figure 9:
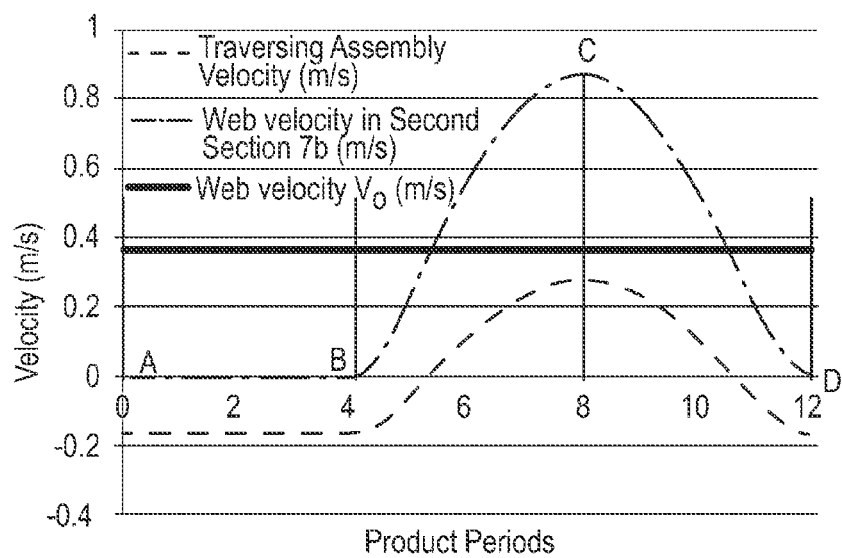
FIG. 9 is a graph of the velocity v. product period for the traversing assembly and one or more webs in accordance with one non-limiting embodiment of the present invention.

The present apparatus 10 can process at least two or more products 36 positioned adjacent to one another in the machine direction MD. Thus, the product period can be at least the time necessary to process two products 36 that are adjacent to one another in the machine direction MD. One of ordinary skill in the art would understand that products 36 may be arranged in any number of ways on the web 12 for processing according to the present disclosure. The products 36 illustrated in FIGS. 6A and 6B are a mere representation of the number and configuration of two or more products 36 on a web 12. One of ordinary skill in the art would understand that, the operation cycle time can increase based on the number of products being acted upon by the processing station 18. The dwell time can be greater than one product period if two or more products 36 are processed in an operation cycle. Further, to process one or more products 36, the peak velocity, indicated by C in FIG. 7, can be greater than two times the initial velocity $V_0$ of the one or more webs 12 on the in-feed side 4 of the apparatus 10. The peak velocity is the maximum velocity reached in a given time period, as illustrated in FIGS. 7 and 9. Referring to FIG. 7, for example, the peak velocity indicated by C is the maximum velocity reached during the return time, from the fourth product period to the sixth produce period.

In another example embodiment, the processing station 18 can be configured to process a three by four product 36 array (total of twelve products 36), as shown in FIG. 6B. Similar to the above, the operation cycle can be governed by the number of products produced in a given time, referred to as the manufacturing line speed. The manufacturing line speed can be used to determine the product period, which is the time required to produce one product in an operation cycle. The manufacturing line speed can be any speed set by the manufacturing operator and obtainable by the manufacturing line. In this example embodiment, the line speed can be 600 parts per minute, which is equal to ten products per second or 0.1 seconds per product. Thus, the product period is 0.1 seconds per product. Since the total number of products to be processed by the processing station 18 is twelve, the cycle time of the operation cycle will be the number of products (12) multiplied by the product period (0.1 seconds per product). Thus, the operation cycle must complete in a cycle time of 1.2 seconds to maintain the integrity of the web(s) 12 downstream of the out-feed side 6 of the apparatus 10. Failure to complete the web(s) processing within the cycle time of the operation cycle could result in a strained, torn, or damaged web 12.

Figure 10:
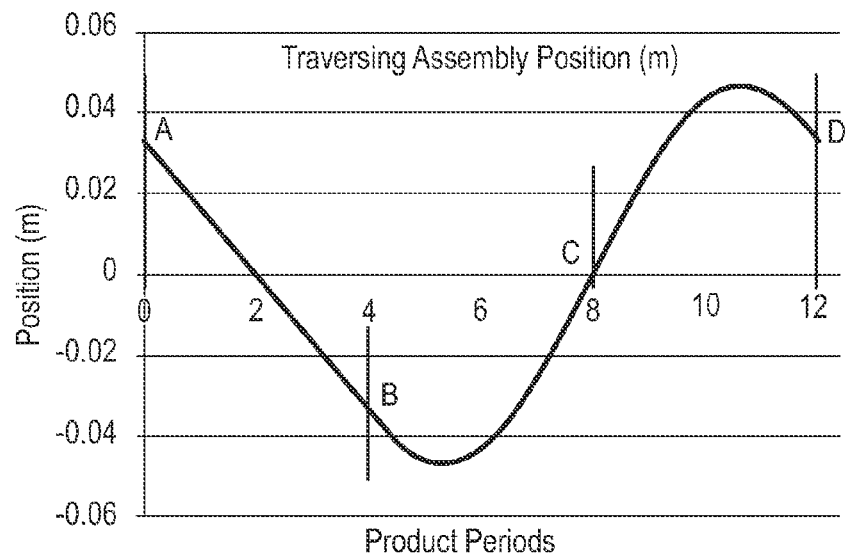
FIG. 10 is a graph of the position of the traversing assembly at a given product period in accordance with one non-limiting embodiment of the present invention.

FIG. 9 shows the velocity profiles of the first traversing guide 14 and the second traversing guide 16, and the one or more webs 12 to process the array of twelve products (as shown in FIG. 6B). As previously stated the bonding time is a predetermined time. In the instant example embodiment, the bonding time can be four product periods (which is equivalent to 0.4 seconds). Thus, the first traversing guide 14 and the second traversing guide 16, operatively connected by the sled 24, can be controlled such that the one or more webs 12 dwell in second section 7b for at least the bonding time. More specifically, the sled 24 operatively engaging the first traversing guide 14 and the second traversing guide 16 can be moved in a first direction FD to dwell the one or more webs 12 for the predetermined bonding time in second section 7b. Once the processing of the one or more webs is complete, the end of the bonding time, the traversing assembly 8 can move in a second direction SD such that the one or more webs 12 are accelerated out of the area of the one or more processing stations 18. The return time is the time remaining for the traversing assembly 8 to return to the start position 39. In the instant example embodiment, the return time is equal to the cycle time of the operation cycle minus the bonding time. Thus, the return time is equal to eight product periods (0.8 seconds). The position of the traversing assembly 8, is shown in FIG. 10. The traversing assembly 8 must be accelerated and decelerated such that the traversing assembly 8 has returned to the start position 39 in the return time.

More specifically, still referring to FIGS. 9 and 10, the traversing assembly 8 beings an operation cycle at a start position 39 (not shown, for example, in FIG. 5), which can be the position at which the traversing assembly changes direction. The velocity of the traversing assembly 8 in the start position 39 is about zero and, thus, the velocity of the web in second section 7b is about equal to the velocity of the one or more webs 12 in the upstream trajectory 3, which is $V_0$ (referred to as the first velocity). Once the operation cycle begins, the traversing assembly 8 can move in a first direction FD at a second velocity sufficient to take up the one or more webs entering through the in-feed side 4 of the apparatus 10 and to dwell, or render stationary, the one or more webs in second section 7b. The traversing assembly 8 can move in the first direction FD at the second velocity for the bonding time. At the end of the bonding time, the traversing assembly 8 will decelerate to reach zero. At the time of the traversing assembly 8 is decelerating, the one or more webs 12 will begin to accelerate in the second section 7b. Upon reaching zero, the traversing assembly 8 can change direction to move in a second direction, opposite the first direction. After the change in direction, the traversing assembly can accelerate, which accelerates the one or more webs 12 in the second section 7b to greater than two times $V_0$. The traversing guide 8 will then begin to decelerate as it approaches the start position 39. During the deceleration of the traversing assembly 8, the one or more webs 12 also decelerate. However, at the end of the deceleration the traversing assembly 8 can be in a position other than the start position 39, as shown in FIG. 8. Thus, the traversing assembly 8 will be accelerated back to the start position 39. When the traversing assembly has reached the start position 39, the one or more webs 12 in second section 7b can again reach a velocity of $V_0$. In general if the dwell time is at least one-half of the cycle time of the operation cycle, then the one or more webs 12 in second section 7b will reach a velocity greater than $2 V_0$.

As stated above, to process one or more products 36, the peak velocity, indicated by C in FIGS. 7 and 9, can be greater than two times the initial velocity $V_0$ of the one or more webs 12 on the in-feed side 4 of the apparatus 10. Thus, the equipment selected to drive the sled 24 and/or the first traversing guide 14 and the second traversing guide 16 can have the ability to handle fast speeds and quick changes in direction. A motor that directly drives the sled 24 only in a substantially sinusoidal profile, as shown in FIG. 3, would be inadequate for an apparatus 10 that can be required to dwell the one or more webs 12 for a time longer than one product period. The operation of such a motor allows the one or more webs 12 to dwell for a moment in time per operation cycle. One of skill in the art would understand that using such a motor would not be economical or feasible for the embodiments disclosed having an apparatus 10 that processes more than one product 36 in an operation cycle and, thus, must dwell for more than a moment in time.

By contrast, any actuator device 60, which allows for motion to be translated into linear motion in a non-sinusoidal velocity profile, can be used to drive the first traversing guide 14 and the second traversing guide 16, and/or the sled 24. Thus, rotary actuators and linear actuators can be utilized to drive the first traversing guide 14 and the second traversing guide 16, and/or the sled 24, in a non-sinusoidal velocity profile. Actuator devices 60 can be powered pneumatically, hydraulically, or electrically. For example, electronically powered, linear motor drive, such as a servo motor 61, which allows for precise control of velocity and position can be used to drive the apparatus 10 such that one or more webs 12 can dwell for longer than one product period, as shown in the velocity profiles of FIGS. 7 and 9.

Figure 11:
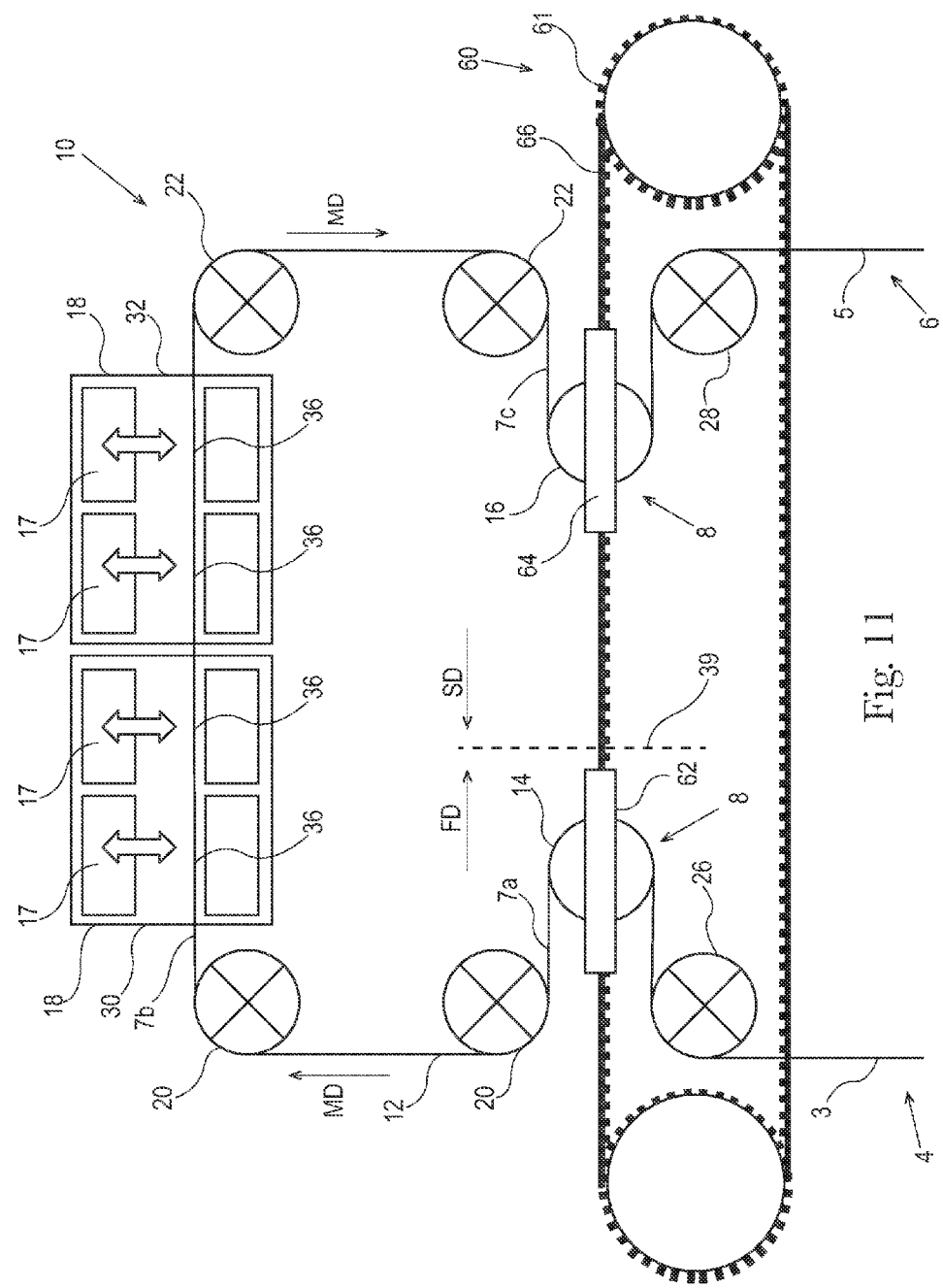
FIG. 11 is a schematic representation of an apparatus to dwell and process one or more webs in accordance with one non-limiting embodiment of the present invention.

More specifically, in one example embodiment shown in FIG. 11, a servo motor 61 can operatively connect to a belt 66 that operatively engages and drives a first shuttle 62 and a second shuttle 64. The first shuttle 62 can removably attach to the first traversing guide 14 and the second shuttle 64 can removably attach to the second traversing guide 16. Any connection means can be used to attach the shuttles so long as the connection allows the shuttles 62, 64 to control the position and velocity of the guides 14, 16 during an operation cycle. For example, the shuttles 62, 64 can be removably attached to the first traversing guide 14 and the second traversing guide 16 by a mechanical device such as a screw or clamp.

Further, the servo motor 61 can be sized to move the first traversing guide 14 and the second traversing guide 16 to a certain position in allotted predetermined time period, as shown in the example velocity profiles of FIGS. 7 and 9. A servo motor 61, in effect, can precisely repeatedly stop and reverse rotary motion to drive the first traversing guide 14 and the second traversing guide 16 in a velocity profile such as those depicted in FIGS. 7 and 9. The sizing of the servo motor 61 can depend on other characteristics of the apparatus 10. More specifically, the sizing of the servo motor 61 can depend on the mass of the traversing assembly 8 that can comprise a first shuttle 62, a first traversing guide 14, a second shuttle 64, and a second traversing guide 16, and the movement profile required to dwell the one or more webs.

The actuator device 60, such as a servo motor 61, can engage with a belt 66 that engages the traversing assembly 8. The traversing assembly can comprise a first shuttle 62 and a second shuttle 64. The belt 66 can engage at least a portion of the first shuttle 62 and the second shuttle 64. For example, in one embodiment, the belt 66 can comprise one or more teeth. The one or more teeth can engage with at least a portion of the first shuttle 62 and the second shuttle 64 and control the movement of at least one of the first shuttle 62 and the second shuttle 64. Further, a portion of the first shuttle 62 and a portion of the second shuttle 64 can connect to the first traversing guide 14 and the second traversing guide 16, respectively. More specifically, when the one or more processing stations 18 acts to process the one or more webs 12, the actuator device 60, such as a servo motor 61, can be used to move each of the first shuttle 62 and the second shuttle 64 in a first direction FD (the machine direction of the web in second section 7b) at the appropriate velocity to dwell the one or more webs 12 in second section 7b. Similarly, upon completing the processing of two or more products during bonding time and after the completion of the dwell time, the actuator device 60 can once again engage the first shuttle 62 and the second shuttle 64 to move the first traversing guide 14 engaged with the first shuttle 62 and the second traversing guide 16 engaged with the second shuttle 64 in a second direction SD back to the start position 39 in the return time. The servo motor 61 facilitates the cyclic acceleration and deceleration of the traversing assembly 8 in the allotted return time.

Figure 12:
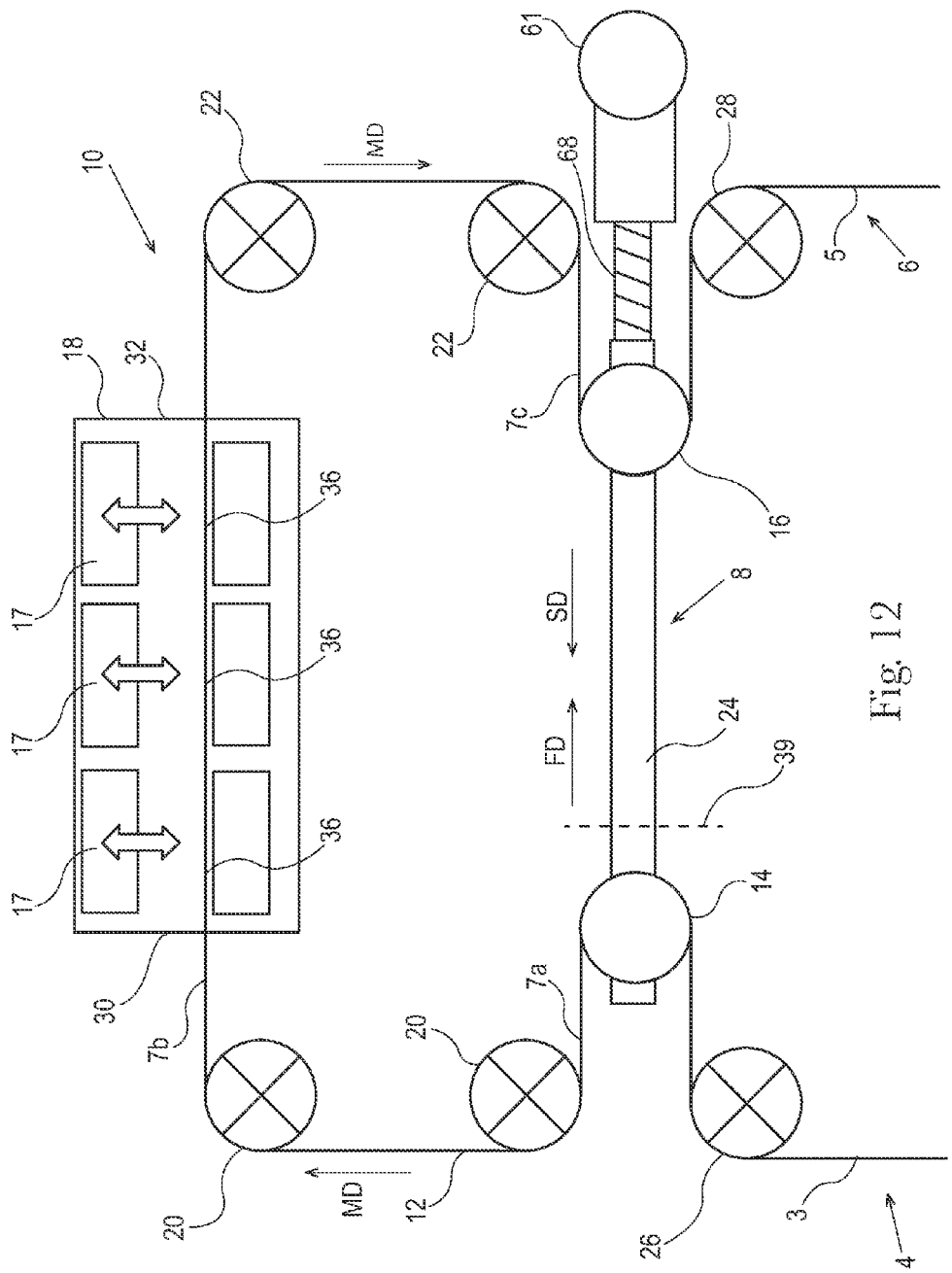
FIG. 12 is a schematic representation of an apparatus to dwell and process one or more webs in accordance with one non-limiting embodiment of the present invention.

In another example embodiment, a servo motor 61 or other actuator device 60 can be used to engage the traversing assembly 8, which can comprise at least one of the sled 24, the first traversing guide 14, and the second traversing guide 16, with a linear spindle 68. In one example embodiment, the linear spindle 68 can be used to move the sled 24, operatively engaged with the first traversing guide 14 and the second traversing guide 16, as shown in FIG. 12. The linear spindle 68 can be connected to a servo motor 61 or other actuator device. The servo motor 61 drives the linear spindle 68 such that the linear spindle 68 extends and retracts driving the sled 24 at a desired velocity and to a desired position. An example of a linear spindle drive 68 suitable to transport the traversing assembly 8 can be the RS Actuator Series available from Misumi Corporation. One of ordinary skill in the art would understand that one or more actuator devices 60 can be used to drive the linear spindle such that it operatively engages the sled and/or independent shuttles of the traversing assembly 8.

Figure 13:
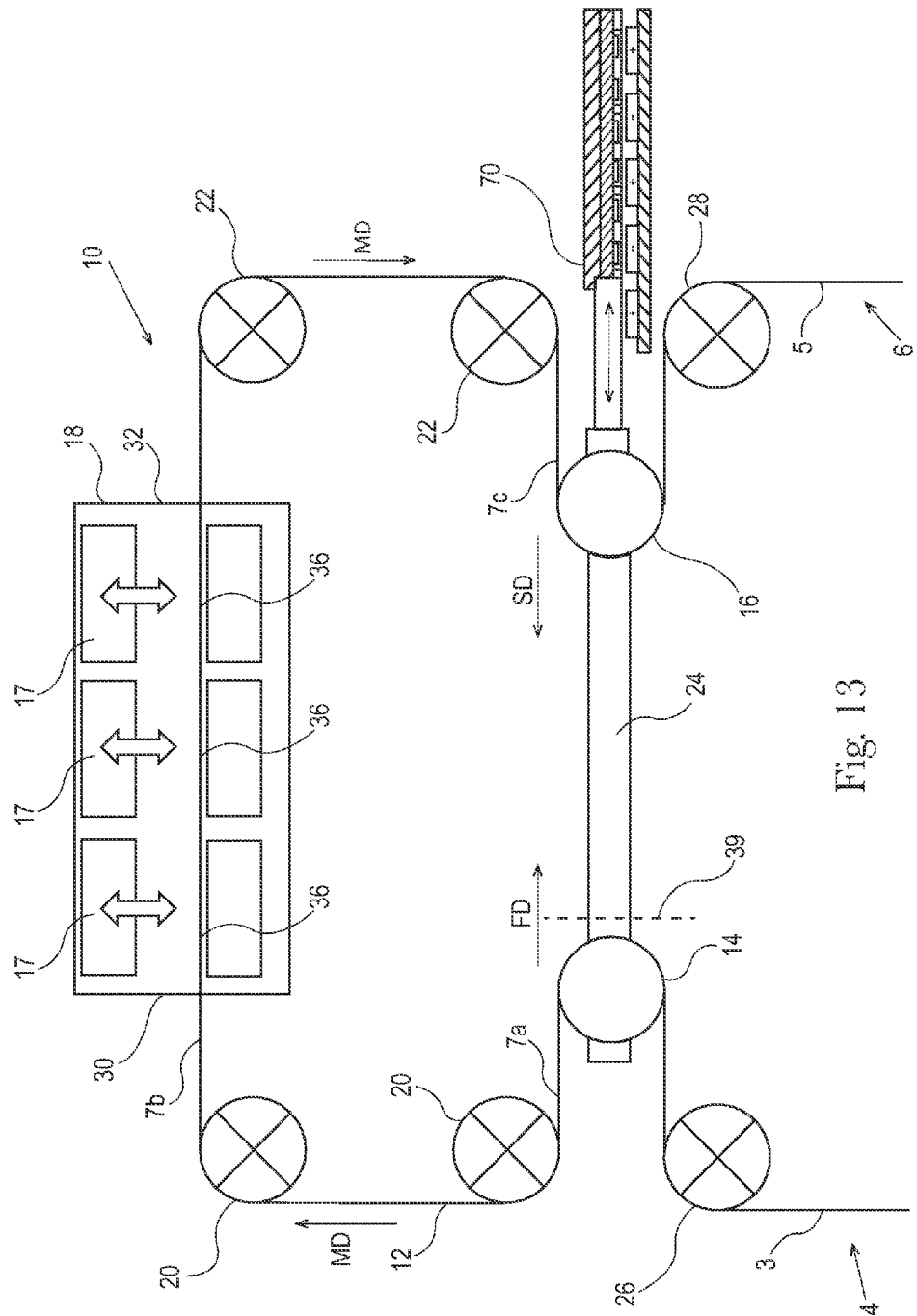
FIG. 13 is a schematic representation of an apparatus to dwell and process one or more webs in accordance with one non-limiting embodiment of the present invention.

In another example embodiment, a linear motor drive 70 can be used to drive the sled 24, operatively engaging the first traversing guide 14 and the second traversing guide 16, as shown in FIG. 13. The linear motor drive 70 can be used to move the sled 24, operatively engaged with the first traversing guide 14 and the second traversing guide 16. The linear motor drive 70 extends and retracts driving the sled 24 at a desired velocity and to a desired position. Such a linear motor drive 70 suitable to drive the sled 24 is the Iron Core Linear Motor Products, LC100 available from Rockwell Automation. One of ordinary skill in the art would understand that one or more linear motor drives 70 can be used to drive the sled and/or independent shuttles of the traversing assembly 8.

Further to the above, an actuator device 60 can be used to drive the first traversing guide 14 and the second traversing guide 16 independently of one another. However, as stated, there must be some operative connection between the first traversing guide 14 and the second traversing guide 16, such as an electrical connection, to keep the two guides in relative fixed position with one another during the operation cycle. An example embodiment is depicted schematically in FIG. 14.

Figure 14:
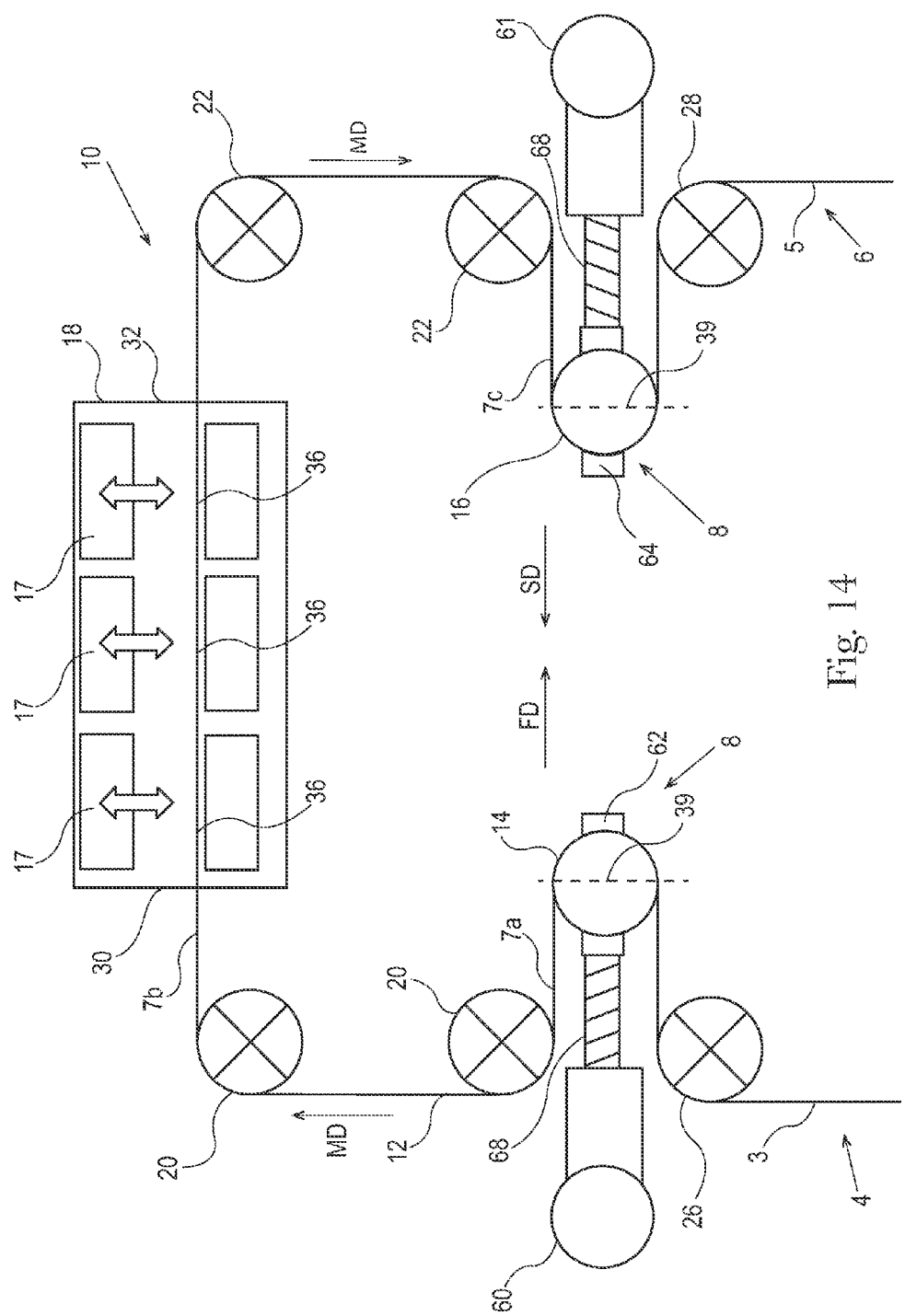
FIG. 14 is a schematic representation of an apparatus to dwell and process one or more webs in accordance with one non-limiting embodiment of the present invention.

FIG. 14 illustrates two linear spindle drives 68, each operatively engaged with one of a first shuttle 62 and a second shuttle 64. The first shuttle can be connected to the first traversing guide 14 and the second shuttle 64 can be connected to the second traversing guide 16. A control unit (not shown) disposed within or on each linear spindle drives 68 can be in communication with one another such that each drive remains synchronized during the operation cycle. Where the first traversing guide 14 and the second traversing guide 16 are each removably connected to a first shuttle 62 and a second shuttle 64, respectively, each of the first traversing guide 14 and the second traversing guide 16 has a start position 39, as shown in FIG. 14. Thus, at the end of the operation cycle, the first traversing guide 14 returns to a start position 39, which is the position of the first traversing guide 14 just prior to beginning an operation cycle, and the second traversing guide 16 returns to a different start position 39, which is the position of the second traversing guide 16 just prior to beginning an operation cycle. Stated another way, each traversing guide 14, 16 can have an start position 39 when being driven independently and the start position 39 can be the position in which each traversing guide starts the operation cycle.

Figure 15:
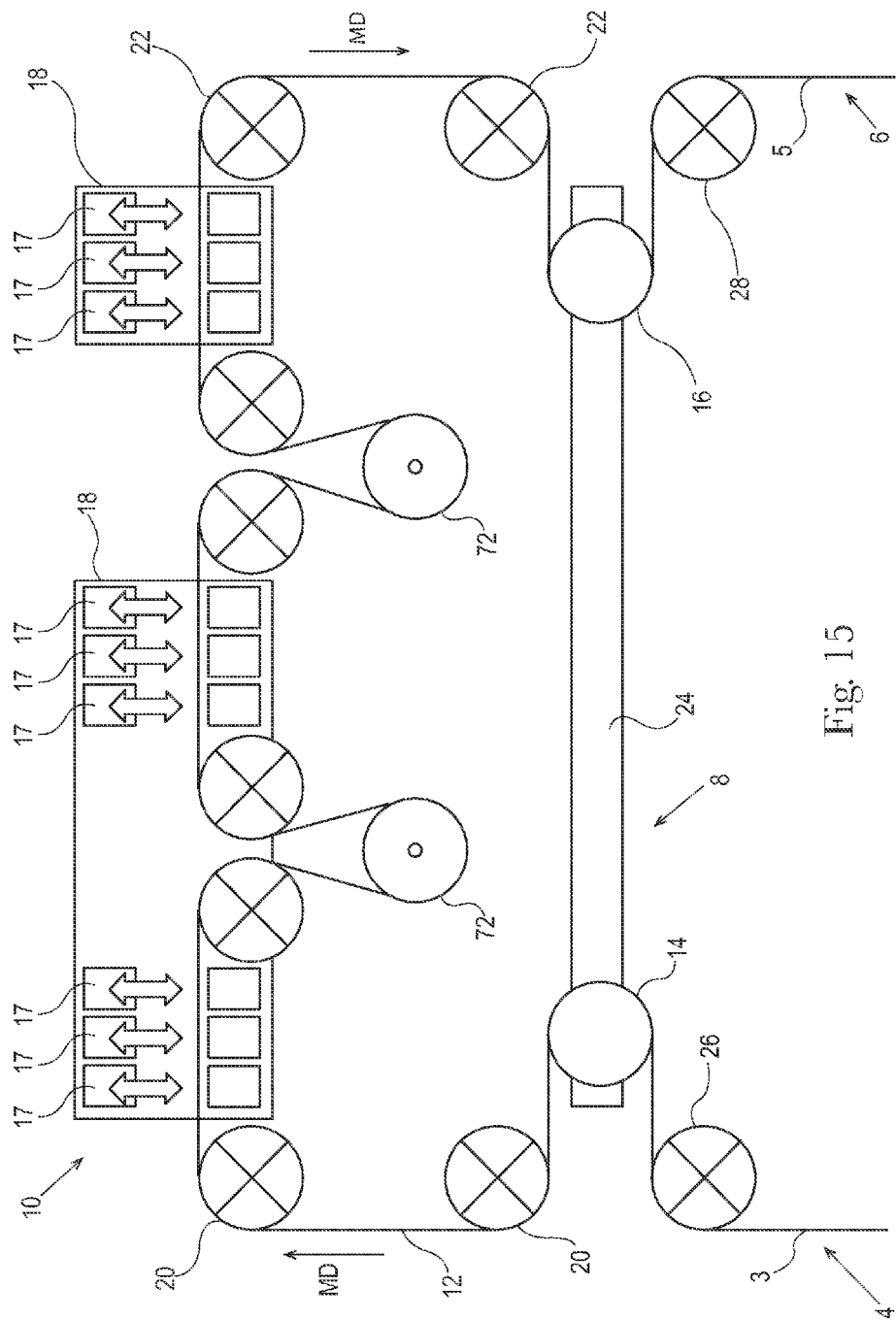
FIG. 15 is a schematic representation of an apparatus to dwell and process one or more webs in accordance with one non-limiting embodiment of the present invention.
Figure 16:
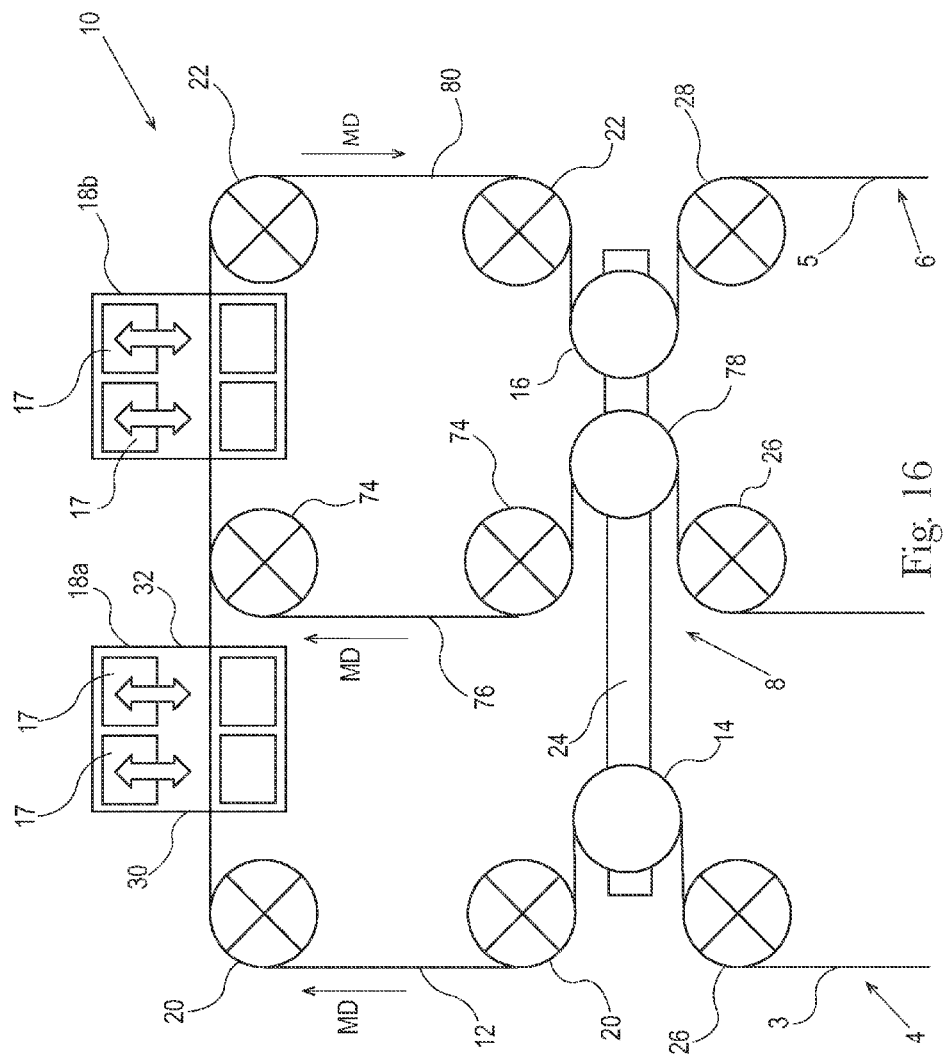
FIG. 16 is a schematic representation of an apparatus to dwell and process one or more webs in accordance with one non-limiting embodiment of the present invention.
Figure 17:
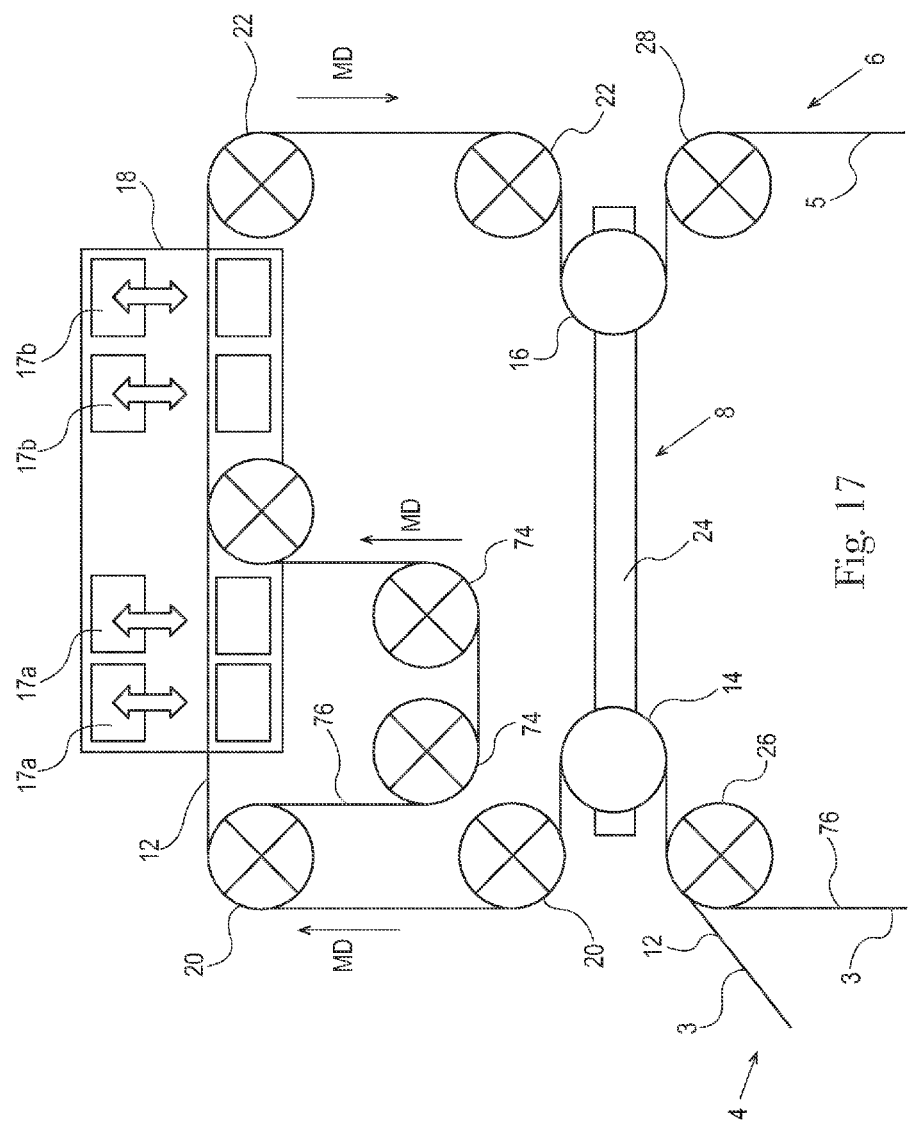
FIG. 17 is a schematic representation of an apparatus to dwell and process one or more webs in accordance with one non-limiting embodiment of the present invention.

The apparatus 10 of the present disclosure can be configured in a number of ways to process different types of products 36. For example, certain products 36 may need to be processed such that a portion of the product 36 does not need to undergo processing. Similarly, a product 36 may need to be manufactured in a way that one or more processes need to be completed sequentially and independently of one another. Still further, a product 36 may need to be processed such that alignment of the webs 12 prior to processing becomes important. FIGS. 15-17 illustrate various configurations of the apparatus 10 that can accommodate different product 36 processing.

FIG. 15 illustrates an example embodiment of an apparatus 10 to process one or more products 36 during an operation cycle. More specifically, the apparatus 10 can compensate for variable length products 36 and/or products 36 comprising an unprocessed portion. To compensate for these types of products 36, the apparatus 10 comprises one or more pitch guides 72. A pitch guide 72 can be any device about which a web 12 can wrap and be transported. The pitch guides 72 can be positioned to set the pitch between products being processed. That is, each pitch guide 72 can be adjusted and positioned in a manner to increase or decrease the length in the one or more webs 12 between adjacent processing stations 18.

FIG. 16 schematically shows another example embodiment of an apparatus 10 that can process layers of one or more webs 12 during an operation cycle. The apparatus 10 can be configured such that one or more webs 12 enter into and are processed by a first processing station 18a and are subsequently joined by one more webs 76 before being processed in a second processing station 18b. The apparatus 10 can comprise one or more intermediate variable speed guides 74 that can direct the one or more webs 76 to join the one or more webs 12, directed by the first variable speed guide 20 and processed in a processing station 18b. After processing the one or more webs 12 and 76 in second processing station 18b, multi-web 80 can be directed by the second variable speed guides 22 to the out-feed side 6 of the apparatus 10. Further to the above, a third traversing guide 78 can be added to the apparatus 10 such that the one or more webs 76 can be moved appropriately during the operation cycle. One of ordinary skill in the art would understand that any number of intermittent variable speed guides can be added to guide any number of subsequent webs.

Another example apparatus 10 that can be used to join and disjoin one or more webs is illustrated schematically in FIG. 17. The apparatus 10 can be configured such that two sets of one or more webs 12, 76 enter the in-feed side 3 of the apparatus 10. The two sets of one or more webs 12, 76 can be conveyed in such a way that one or more webs 12 can be placed in face to face relation to one or more webs 76. The one or more webs 12, 76 can be conveyed such the products 36 of the one or more webs 12 are placed in a predetermined face to face relationship to the products 36 of one or more webs 76. Further, by conveying the one or more webs 12, 76 at the in-feed side 3 of the apparatus 10 allows a first traversing guide 14 and a second traversing guide 16 to control the movement and position of both of the one or more webs 12, 76 together. Thus, both of the one or more webs 12, 76 can be wrapped around the first traversing guide 14, which can control the movement of the one or more webs 12, 76 downstream of the first traversing guide 14. The one or more webs 12 can dwell for the same period of time at the same points in time as the one or more webs 76. Prior to entering a processing station 18, one or more webs 12 can be disjoined from the other one or more webs 76 such that only the one or more webs 12 enter the processing station 18. The one or more webs 12 can be processed by one or more processing units 17a while the one or more webs 76 are routed around the one or more processing units 17a. The other one or more webs 76 can be guided by intermittent variable speed guides 74 around the processing units 17a. After the one or more webs 12 have completed processing by the processing station 18, the one or more webs 12 can again be joined to the one or more webs 76. The one or more webs 12, 76 can then be processed by a processing units 17b. After completion of all processing units within the processing station 18, the web 80 can be moved toward out-feed side 5 of the apparatus 10.

In another example embodiment, as illustrated in FIG. 18, the processing station 18 can comprise a first pathway 98 with one or more first processing units 17a and a second pathway 100 comprising one or more second processing units 17b, which can be adjacent to the first one or more processing units 17a. As described above, the one or more webs 12 can be controlled by at a first traversing guide 14 (not shown). After being transferred from at least one of the first traversing guide 14 and the first variable speed guide 20, the one or more webs 12 can enter the processing station 18 through an entrance 90. A predetermined length of web 12 can be fed through the entrance 90. The predetermined length of web 12 in the area of the one or more first processing units 17a is the first process pitch 84. One of ordinary skill in the art would readily understand that the dimensions of the processing station 18 can be dictated by the process pitch 84. The one or more webs 12 can then dwell for the predetermined dwell time. During the dwell, the one or more first processing units 17a can act on the one or more webs 12. As illustrated in FIG. 18, the number of products 36 does not have to equal the number of processing units 17. Stated another way, one processing unit 17a, 17b can bond more than one product 36 simultaneously. For example, each of the one or more first processing stations 17a can be an ultrasonic horn, and each ultrasonic horn can bond four products simultaneously.

Still referring to FIG. 18, while the one or more first processing units 17a processes the first process pitch 84, a second process pitch 86 can be located between the intermediate exit 92 of the one or more first processing units 17a and the intermediate entrance 94 of the one or more second processing units 17b. The length of the second process pitch 86 can be equal to the length of the one or more webs 12 between the intermediate exit 92 of the one or more first processing units 17a and the intermediate entrance 94 of the one or more second processing units 17b. The second process pitch 86 can be arranged such the one or more webs 12 are suspended between one or more turn bars 82. The length of the first process pitch 84 can be substantially equal to the length of the second process pitch 86. Similar to the above, a third process pitch 88 can be located in the area of the one or more second processing units 17b. The length of the third process pitch 88 can be equal to the length of the one or more webs 12 between the intermediate exit 92 and the processing station exit 96. The length of the third process pitch 88 can be equal to the length of at least one of the first process pitch 84 and the second process pitch 86. By having the first process pitch 84, second process pitch 86, and third process pitch 88 of substantially equal length, the one or more webs 12 can be indexed and can be rendered stationary such that the one or more first processing units 17a act on the same length of the one or more webs 12 as the one or more second processing units 17b.

While the one or more first processing units 17a process the first process pitch 84 of the one or more webs 12, the one or more second processing units 17b can processes the third process pitch 88 of the one or more webs 12. One of ordinary skill in the art would recognize that the second process pitch 86 of the one or more webs 12 can dwell simultaneously with the first process pitch 84 and third process pitch 88 of one or more webs 12. Thus, another process can be added that performs some process on the second process pitch 86 of one or more webs 12. Further, one or more turn bars 82 can be added to direct the one or more webs 12 through an added process. For example, a second processing station 18 can be added in the area of the second process pitch 86. Alternatively, a processing station 18 can be designed to include one or more third processing units to process the second process pitch 86 of one or more webs 12 (not shown).

Still referring to FIG. 18, the one or more turn bars 82 can be adjusted to account for different process pitches. Further, the processing station 18 can be divided up into more than one processing station 18 (not shown), such that the first processing station 18 can comprise one or more first processing units 17a and a second processing station 18 can comprise one or more second processing units 17b. Still further, a second set of one or more turn bars 82 (not shown) can be located adjacent to the processing station exit 96 such that the one or more webs 12 can be directed to enter a subsequent processing station 18 (not shown). One of ordinary skill in the art would readily recognize that a number of turn bars and processing stations can be placed in series to perform numerous processes on the one or more webs 12.

Any type of processing station 18 configured to bond one or more webs 12 can be suitable for the present disclosure. More specifically, for example, a device such as that disclosed in European Patent No. 2105281 can be used as the processing station 18 to process the one or more webs 12.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing a localized dwell in a portion of a web, the method comprising:
    conveying one or more webs at a first velocity in a machine direction, wherein the one or more webs are conveyed by an apparatus comprising a first traversing guide and a second traversing guide, wherein the first traversing guide and the second traversing guide are operatively connected in a fixed spatial relationship, and wherein the first traversing guide and the second traversing guide are moveable from a start position in a substantially linear path, and wherein the first traversing guide and the second traversing guide return to the start position after an operation cycle in a cycle time;
    moving the first traversing guide and the second traversing guide in a first direction at a second velocity equal to about one half the first velocity for a dwell time;
    bonding the one or more webs, wherein the bonding is performed at one or more processing stations;
    accelerating and decelerating the first traversing guide and the second traversing guide in a second direction opposite the first direction until the first traversing guide and the second traversing guide are returned to the start position in a return time, wherein the return time equal to the difference between the cycle time and the dwell time, and wherein the dwell time is greater than one product period.

2. The method of claim 1, wherein the first traversing guide and the second traversing guide are moving in the first direction while the one or more processing stations are bonding the one or more webs.

3. The method of claim 1, wherein a peak velocity of the one or more webs during the return time is greater than twice the first velocity.

4. The method of claim 1, comprising bonding the one or more webs to another layer of one or more webs.

5. The method of claim 1, wherein the one or more webs travels from the first traversing guide to the second traversing guide.

6. The method of claim 1, wherein the one or more webs comprise two or more products and wherein at least one of the two or more products is adjacent to another of the two or more products in the machine direction.

7. The method of claim 1, wherein the dwell time is greater than the return time.

8. The method of claim 1, wherein the two or more products are bonded in the cycle time.

9. The method of claim 1, wherein bonding is by ultrasonic bonding.

10. The method of claim 1, wherein the bonding is by a processing station comprising two or more processing units, wherein the two or more processing units comprise ultrasonic horns.

11. The method of claim 10, wherein the number of ultrasonic horns included in the processing station is less than the number of the two or more products on the one or more webs.

12. The method of claim 1, wherein the bonding is by thermal bonding.

13. The method of claim 1, wherein the first traversing guide and the second traversing guide are mechanically connected and driven by the same actuator device.

14. The method of claim 1, wherein the first traversing guide and the second traversing guide are electrically connected and driven by different actuator devices.

15. The method of claim 1, wherein the apparatus comprises one or more first variable speed guides and one or more second variable speed guides operatively engaging the one or more webs.

16. The method of claim 1, wherein the apparatus comprises one or more first fixed guides and one or more second fixed guides operatively engaging the one or more webs.

17. The method of claim 1, wherein three or more webs are bonded.

18. The method of claim 1, wherein the first traversing guide and the second traversing guide are operatively engaged by a sled, wherein the sled is driven by an actuator device.

19. A method for producing a localized dwell in a portion of a web, the method comprising:
    conveying one or more webs at a first velocity in a machine direction, wherein the one or more webs are conveyed by an apparatus comprising a traversing assembly and at least one processing station adjacent to the traversing assembly, wherein the traversing assembly is moveable from a start position in a substantially linear path, and wherein the traversing assembly returns to the start position after an operation cycle in a cycle time, and wherein the one or more webs comprise a second section in the area of the at least one processing station;

moving the traversing assembly at a second velocity sufficient to dwell the second section of the one or more webs for a dwell time;

bonding layers of the one or more webs, wherein the bonding is performed at the one or more processing stations;

accelerating and decelerating the traversing assembly in a second direction opposite the first direction until the traversing assembly is returned to the start position in a return time, wherein the return time equal to the difference between the cycle time and the dwell time, and wherein the dwell time is greater than the return time.

20. A method for producing a localized dwell in a portion of a web, the method comprising:

conveying one or more webs at a first velocity in a machine direction, wherein the one or more webs are conveyed by an apparatus comprising a traversing assembly and at least one processing station adjacent to the traversing assembly, wherein the traversing assembly is moveable from a start position in a substantially linear path, and wherein the traversing assembly returns to the start position after an operation cycle in a cycle time, and wherein the one or more webs comprise a second section in the area of the at least one processing station;

moving the traversing assembly at a second velocity sufficient to dwell the second section of the one or more webs for a dwell time;

bonding at least two layers of the one or more webs, wherein the bonding is performed at the one or more processing stations;

decelerating the traversing assembly from the second velocity to a third velocity, wherein the third velocity is equal to zero, and wherein the one or more webs travels at a first velocity when the traversing assembly is at the third velocity;

accelerating the traversing assembly in a second direction opposite the first direction, and wherein the one or more webs reach a velocity of greater than at least two times the first velocity;

decelerating the traversing assembly moving in the second direction until the traversing assembly reaches the third velocity, and wherein the one or more webs travel at a first velocity when the traversing assembly is at the third velocity;

accelerate the traversing assembly in the first direction to the second velocity until the traversing assembly reaches the start position, and wherein the traversing assembly returns to the start position in a return time, wherein the return time is equal to the difference between the cycle time and the dwell time, and wherein the dwell time is greater than one product period.

* * * * *